US011505801B2

(12) United States Patent
Chen et al.

(10) Patent No.: US 11,505,801 B2
(45) Date of Patent: Nov. 22, 2022

(54) *AGROBACTERIUM TUMEFACIENS* STRAINS

(71) Applicant: SYNGENTA PARTICIPATIONS AG, Basel (CH)

(72) Inventors: Zhongying Chen, Research Triangle Park, NC (US); Qiudeng Que, Research Triangle Park, NC (US); Mark Scott Rose, Research Triangle Park, NC (US); Heng Zhong, Research Triangle Park, NC (US); Mary-Dell Chilton, Research Triangle Park, NC (US); Eric Levy, Research Triangle Park, NC (US); Yingping Lucy Qin, Research Triangle Park, NC (US)

(73) Assignee: Syngenta Participations AG, Basel (CH)

( * ) Notice: Subject to any disclaimer, the term of this patent is extended or adjusted under 35 U.S.C. 154(b) by 39 days.

(21) Appl. No.: 16/634,207

(22) PCT Filed: Jul. 26, 2018

(86) PCT No.: PCT/US2018/043856
§ 371 (c)(1),
(2) Date: Jan. 27, 2020

(87) PCT Pub. No.: WO2019/027790
PCT Pub. Date: Feb. 7, 2019

(65) Prior Publication Data
US 2020/0208162 A1  Jul. 2, 2020

Related U.S. Application Data

(60) Provisional application No. 62/541,221, filed on Aug. 4, 2017.

(51) Int. Cl.
*C12N 15/82* (2006.01)
*C12N 15/74* (2006.01)
*C12N 15/90* (2006.01)
*C12N 1/20* (2006.01)
*C12R 1/01* (2006.01)

(52) U.S. Cl.
CPC ......... *C12N 15/743* (2013.01); *C12N 1/205* (2021.05); *C12N 15/8205* (2013.01); *C12N 15/902* (2013.01); *C12R 2001/01* (2021.05)

(58) Field of Classification Search
None
See application file for complete search history.

(56) References Cited

U.S. PATENT DOCUMENTS 5,929,306 A * 7/1999 Torisky .............. C12N 15/8205
800/298

OTHER PUBLICATIONS

Palanichelvam et al. (Molecular plant-microbe interactions 13.10 (2000): 1081-1091). (Year: 2000).*
Zhao, et al. (Scientific reports 6.1 (2016): 1-11). (Year: 2016).*
Svitashev et al. (Plant physiology 169.2 (2015): 931-945). (Year: 2015).*
Palanichelvam et al., "A Second T-Region of the Soybean-Supervirulent Chrysopine-Type Ti Plasmid pTiChry5, and Construction of a Fully Disarmed virHelper Plasmid", MPMI, vol. 13, No. 10, 2000, pp. 1081-1091.
Farrand et al., "Construction of an Agrobacterium tumefaciens C58 recA Mutant", Journal of Bacteriology, Oct. 1989, vol. 171, No. 10, pp. 5314-5321.
International Search Report dated Jan. 8, 2019 for International Application No. PCT/US18/43856.
Supplementary European Search Report for EP Application No. 18842192.9 dated Mar. 10, 2021.
Hwang Hau-Hsuan et al: "Agrobacterium-Mediated Plant Transformation: Biology & Applications"; The *Arabidopsis* Book, vol. 15; Jan. 1, 2017; pp. e0186.
Char Si Nian et al: "An Agrobacterium-delivered CRISPR/CAS9 system for high-frequence targeted mutagenesis in maize"; Plant Biotech. Journal; vol. 15(2), pp. 257-268; Feb. 1, 2017.

* cited by examiner

*Primary Examiner* — Charles Logsdon
(74) *Attorney, Agent, or Firm* — Dale Skalla

(57) ABSTRACT

The invention provides three novel disarmed strains of *Agrobacterium tumefaciens* bacteria useful for the transformation of plants. The invention provides three engineered *A. tumefaciens* Chry5 strains or bacterial cells thereof which comprise the Chry5 strain chromosomal background and a disarmed pTiChry5 vector, and methods of using said bacterial strains or cells for transformation of fungal or plant cells, in particular dicot or monocot plant cells, including soybean, maize, wheat, and sugarcane cells. The invention further relates to the transgenic plants created by these methods.

18 Claims, 1 Drawing Sheet
Specification includes a Sequence Listing.

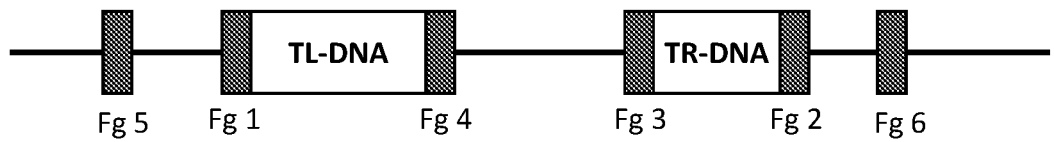

SEQUENCE LISTING

<160> NUMBER OF SEQ ID NOS: 35

<210> SEQ ID NO 1
<211> LENGTH: 5042
<212> TYPE: DNA
<213> ORGANISM: Agrobacterium tumefaciens

<400> SEQUENCE: 1

```
atagtccccg gcatcggttc ttccaaaaat tttacggaag tggtcgcaca aaattccgga       60
catcgcagcg ggtcgaaaag atagtcttta tcaccgcgct ttgccatgct gcatctcagt      120
tgaagggaat ttgctagaca cgaggacgga accagacgaa cgtgaagaat aacacagcga      180
atggcttggt tccatcctcg acgggcagat tgaggtccac ggtgacaagc gcctgacaaa      240
taaactggca atcgccaaat tgtttcccag cgttcactga aatcgactta ccgcacctct      300
gcagcagcgg caggatatat ggcagtgtaa actccatttt cgaacgcggt tcagggcacc      360
tacgattatc gaaaaaggat aacggctgca ggaatatata tgactatgaa aagtgcgggc      420
gttgtggcct tactgggtgt gaaatcgccg tcagtttttg aacttactga acacgtgttt      480
atggcattta gtatagccgt atgcgggatt tccgccttcc gttttgtcag cgggaagccg      540
```

| | |
|---|---|
| cgagacagtg gaatgacccg tactgcaatc tgagcctatg aaagaaacac aaaatcaatc | 600 |
| agcgagagag aaacttttgt ttctctgaat caaaagcgga ccgaggcaat catgccattt | 660 |
| tatcgacttt gagcctgaat tgaagtttat tcgcatcaac gagtaaatac tttaatggtg | 720 |
| attgtaagac gaaataggtt aggcccgtca tgaataccta acaggtccca ctagaaggca | 780 |
| tcttgattta ataaaattgc tcataattca gttaagagcg cgacgatgta ttatgtaccg | 840 |
| ataagaccgt aaattattct gggcaattgt cgaatgaaat tatttcgaat tttatctgct | 900 |
| gaaataattt cgcaatacat tataatataa gataaatgtc tgaaaacaat acatagtccc | 960 |
| atgtcaaatt acaaagcaag tgaacggtgc atacggccga atatgtccga tcttatttga | 1020 |
| tatttgaatt taaagtactc agtattcaga aatacttcaa taactgtgcg cattcgtcaa | 1080 |
| caaaaaatta cgaagcctac tcctcttcag aatcgtagat gtcaaggtga ggtgcctgca | 1140 |
| cgtcgaccct acgtttgacg ccagcgctct tccaagcaag taaagccatg tcgtcctctg | 1200 |
| agcggtcgga aattaccaaa tctggaagat catgcagcag gggtatacca ggcgttcctt | 1260 |
| ggcgacagcg gatgtaatgg cgaaggtcgg tgtcccatgc ttcctctcta ccggtgaaaa | 1320 |
| actcgttatg gaattgcaac cttttttcctt gtgtcacagc actaaaatcg taacttcggg | 1380 |
| taccggtcga gagttttagg tttggtctcg cttcctttat atcgcgatca aactttacat | 1440 |
| agtaagccaa acgcgtgctc gcttcgctag ccctgtacgc gagtctttcg tcttcagttg | 1500 |
| ccgcgtcttc taaagtgtct tcagaaacgt aggacagcat agtttgaaca gcaaaaatgc | 1560 |
| aaatgtcttg ggcgaggacg gaatcaatcc aatattttgc agccccatat atttcatcaa | 1620 |
| cagtcggatg agaatgcccc agatcccttg cgatccgaac catttccatt ggaaaaagca | 1680 |
| taggcatgag gggcacagtc tgcctccatc gaggttccgg atctgcactc tctaccagtt | 1740 |
| gcacaaagtg atccccatca atgtacttga aggtgtagaa tagaagagca accttgccaa | 1800 |
| aatacgccga cctatagctt aaccaggcca cgatgagatg agcttcgtca tcgcggccgt | 1860 |
| cgagaatgaa ggttgcgtcc ggattcacct gaatcgcgct gtcgaggata tcttcaagag | 1920 |
| tgcttatagt ctggtcagta accctgtagt ttgtctcaga gatcttaccg ttctcgatct | 1980 |
| cgcgtatgat gactggtcgt ccaacgatct gatgggacaa aaatttgcga accggcttat | 2040 |
| cctcatctaa agcagcaaca cgaaatacat tgaattcgtg agcgacgatt ggaacgccgt | 2100 |
| ccgccgtgag cgcaatgtca atttcacaaa ggtttctatg cccctctcca atcgcggaca | 2160 |
| aaatagctgt tttcgtacat tcttgaattc cctttcccaa gttaaacatg cctctgtgct | 2220 |
| caacaacctg aacatcgagt ttctcgtcaa gcttctggag cagatttggc gtcgagtaac | 2280 |
| gtgccagcac ttcagagaca cttgttccag cggggagatc ccactctagt tcccacatcg | 2340 |
| gccagttggt atcactccgt cgtctcggct tcctctgaga aagcacctgc aggtaagtta | 2400 |
| atgttgagga ctcacagaaa aataataaaa aaagaaaaat gcctgctcta cctccattgt | 2460 |
| ttatgccgct attttcttaa attgactaga taatattaat agtctgcata ccgaatatat | 2520 |
| ttatagatag ctttacctgt cttattgacg taagcgctta cgttattaac tctgggttct | 2580 |
| aaccaatcga caggtgggcc agtagcatta cggcggtccg tgcaaatgtt cgttgatgcg | 2640 |
| aaaatttgtc tatgctcttc ctgtggatgg gaagttggaa tgtccgcggg tttgcaaagt | 2700 |
| agaaatgtcc gcatgtcacc acacgcaaca ccgaccagcc ccgatctgag cggctgatcc | 2760 |
| cgcttgcaag atcagatcgg ggcgggtgat tgacacacct cttcggcttt agctttgaga | 2820 |
| cgcctcactc cgcagccggc tgttgcgaca gtgctttctt tcgccgcgca atcacaaccg | 2880 |

```
gatcggtcgt gaagtctttc cgacgaccag gtccacgagc gcgtttgatg tatccattct   2940
tatcgctgtt gttcttcacg tcaggcgccg ggcgctcgtc ctgacgctcc ttgatatatg   3000
ccaggacatc accgagccgc ctgttctcgg tgatcgccgc atgcgttacc cgctggtcct   3060
tgtcgaacac ctgatagggc agggaatgtc ccttccatcg cacatccagc cgaccgtccg   3120
cataggcata ggtctcgaca taacggccaa ccaggccacg cgtcaccgcg gtctcctcca   3180
gcatgatccg cttgcgctcg aacgaaaacg tcagctgcga tccgacatag cgctgctcgc   3240
gcttgcacag gatctcagtc aaccgatccg cgccagatt cagcggccga tgcagatcgt    3300
cgggacgggc agggacgatt gcaaaacgcg cgttgtagtc ctctatgaag cccggcaaga   3360
acgcattgcc cgcctgcatg ctgtcgatgc cagaaagcct gagctccttg accaggcgat   3420
cctgcagcgt ccggttcatc cgctcgaccc gaccccttggc ctggctcgaa tttgcacaga  3480
gaatctcgat gtttagctcg cagagcgcac gcccgaactg ggtcatgccc tgaccacccc   3540
tggcatcctt cttcgccacc cggaacactg aatgcttgtc cgaatagaag gcaaccggcg   3600
cgccatgacg cttgagatac agctccaatg cctcgaaata gctgaaggca cttttcgga    3660
gcgcacgaag cgcagctgca tcaacctgcc ggtcgcatcg tcgacaaata ccagcagcga   3720
gcaagacggt ccgcgatcct cgaaccagcg atgctccgag ccgtcgatct gcaccagttc   3780
gccataggct tctcgccgta accgcggctg atgaaacgtc cggcgctgct tgcgcgacag   3840
ccaggggccg gcatcagtca tccagctgcg caccgtctcg cgcgatacac gcagtccatt   3900
gcgctcggcc agcttctccg tcgccaatgt cggcccgaaa tccgcatagc gttcgcgaac   3960
cagcgtcatt gcataatcgc gaaccccggc gctgatccgg ttgttcgacg gccgaccgat   4020
tgccttgtgc cggatcgaag ccgccccgcc agtccgcatg cgctccagca gccggcgcac   4080
ctggcgctcg ctcagatcaa gcacatgcgc cgccgatacc gtggtcatcc ggccggcaac   4140
caccttcgac aaaatctcga tccgttgcag atcgcgctcg ctcatcgcta tcaatcccat   4200
ctgcaatctc ccaggcatcg ttaaggcccg gggagagtga cattccaact ttgaagaatc   4260
aggacacttc aactttgcgg ctacacttcc tgtcgacgta atatcgatta tgagatagcg   4320
ttttccagcc gcttcacgtt cggtgcaatg tagtttcaaa tcatacgcgt taattttcac   4380
tgatgggttg gaggagcaac tggtcgttgc cagaccgcgc cgacggcgtt tcggatcata   4440
cctggggaaa aataagtccg gcaccgagaa cctaatcaat cgcgatttcc atgcaaaagc   4500
gccgaacctg aagtggctga cagatatcac cgggttcaat atcccagccg gaacgtcta    4560
ccttgcgcgc atcatcgact acttcgacgg aacggtcatc agttggtcga ttggatcgca   4620
accagacgcg ggggaatact atgcttgatg cagccattga gaccatgaca gacggcgagg   4680
aacgaccaat cgtccattcc gctcgcggag ctcattatcg ctgggtcggc tggctaatgc   4740
ggattagcga agcaaaccta attcgctcaa tgccccgaag gactgctcac aagataactt   4800
tgcttgtgag gtcttcttct gccggatgaa aacagagctc ttctatcccc gagactggaa   4860
ggctattaga atcgaacagt tcgttgccga gatagacgct tatatccgct ggtacaatga   4920
gaggcgtatt aagatatccc tgggatcact cagcccgatc gaatatcgaa gaagtcttgg   4980
ccctaacttg taaagctgtc caactttta tccacacccc ctccgggtca gttctcaatg    5040
gc                                                                  5042
```

<210> SEQ ID NO 2
<211> LENGTH: 22779
<212> TYPE: DNA
<213> ORGANISM: Agrobacterium tumefaciens

<400> SEQUENCE: 2

```
atagtccccg gcatcggttc ttccaaaaat tttacggaag tggtcgcaca aaattccgga        60
catcgcagcg ggtcgaaaag atagtcttta tcaccgcgct ttgccatgct gcatctcagt       120
tgaagggaat ttgctagaca cgaggacgga accagacgaa cgtgaagaat aacacagcga       180
atggcttggt tccatcctcg acgggcagat tgaggtccac ggtgacaagc gcctgacaaa       240
taaactggca atcgccaaat tgtttcccag cgttcactga aatcgactta ccgcacctct       300
gcagcagcgg caggatatat ggcagtgtaa actccatttt cgaacgcggt tcagggcacc       360
tacgattatc gaaaaaggat aacgctgca ggaatatata tgactatgaa aagtgcgggc        420
gttgtggcct tactgggtgt gaaatcgccg tcagtttttg aacttactga acacgtgttt       480
atggcattta gtatagccgt atgcgggatt ccgccttcc gttttgtcag cgggaagccg        540
cgagacagtg gaatgacccg tactgcaatc tgagcctatg aaagaaacac aaaatcaatc       600
agcgagagag aaacttttgt ttctctgaat caaaagcgga ccgaggcaat catgccattt       660
tatcgacttt gagcctgaat tgaagtttat tcgcatcaac gagtaaatac tttaatggtg       720
attgtaagac gaaataggtt aggcccgtca tgaataccta acaggtccca ctagaaggca       780
tcttgattta ataaaattgc tcataattca gttaagagcg cgacgatgta ttatgtaccg       840
ataagaccgt aaattattct gggcaattgt cgaatgaaat tatttcgaat tttatctgct       900
gaaataattt cgcaatacat tataatataa gataaatgtc tgaaaacaat acatagtccc       960
atgtcaaatt acaaagcaag tgaacggtgc atacggccga atatgtccga tcttatttga      1020
tatttgaatt taaagtactc agtattcaga aatacttcaa taactgtgcg cattcgtcaa      1080
caaaaaatta cgaagcctac tcctcttcag aatcgtagat gtcaaggtga ggtgcctgca      1140
cgtcgaccct acgtttgacg ccagcgctct tccaagcaag taaagccatg tcgtcctctg      1200
agcggtcgga aattaccaaa tctggaagat catgcagcag gggtatacca ggcgttcctt      1260
ggcgacagcg gatgtaatgg cgaaggtcgg tgtcccatgc ttcctctcta ccggtgaaaa      1320
actcgttatg gaattgcaac cttttttcctt gtgtcacagc actaaaatcg taacttcggg      1380
taccggtcga gagttttagg tttggtctcg cttcctttat atcgcgatca aactttacat      1440
agtaagccaa acgcgtgctc gcttcgctag ccctgtacgc gagtctttcg tcttcagttg      1500
ccgcgtcttc taaagtgtct tcagaaacgt aggacagcat agtttgaaca gcaaaaatgc      1560
aaatgtcttg ggcgaggacg gaatcaatcc aatattttgc agccccatat atttcatcaa      1620
cagtcggatg agaatgcccc agatcccttg cgatccgaac catttccatt ggaaaaagca      1680
taggcatgag gggcacagtc tgcctccatc gaggttccgg atctgcactc tctaccagtt      1740
gcacaaagtg atccccatca atgtacttga aggtgtagaa tagaagagca accttgccaa      1800
aatacgccga cctatagctt aaccaggcca cgatgagatg agcttcgtca tcgcggccgt      1860
cgagaatgaa ggttgcgtcc ggattcacct gaatcgcgct gtcgaggata tcttcaagag      1920
tgcttatagt ctggtcagta accctgtagt ttgtctcaga gatcttaccg ttctcgatct      1980
cgcgtatgat gactggtcgt ccaacgatct gatgggacaa aaatttgcga accggcttat      2040
cctcatctaa agcagcaaca cgaaatacat tgaattcgtg agcgacgatt ggaacgccgt      2100
ccgccgtgag cgcaatgtca atttcacaaa ggtttctatg cccctctcca atcgcggaca      2160
aaatagctgt tttcgtacat tcttgaattc cctttcccaa gttaaacatg cctctgtgct      2220
caacaacctg aacatcgagt ttctcgtcaa gcttctggag cagatttggc gtcgagtaac      2280
```

```
gtgccagcac ttcagagaca cttgttccag cggggagatc ccactctagt tcccacatcg    2340
gccagttggt atcactccgt cgtctcggct tcctctgaga aagcacctgc aggtaagtta    2400
atgttgagga ctcacagaaa aataataaaa aaagaaaaat gcctgctcta cctccattgt    2460
ttatgccgct attttcttaa attgactaga taatattaat agtctgcata ccgaatatat    2520
ttatagatag ctttacctgt cttattgacg taagcgctta cgttattaac tctgggttct    2580
aaccaatcga caggtgggcc agtagcatta cggcggtttg tacgtctctc acagagataat   2640 actatttgat tgttgatttg tttgtaactt gtgttgagtg cacctaaact gcaccccaat    2700
tcgaccggac ggtatgcata agggcataag cagagaggca caggcgtggg tatcggtggc    2760
atccgcagtc tcggagcgcg aggtgcgggg ttcgccgtat aggcgcggga agatcctgat    2820
gtccatctgt actgacaggc ggcccgatct acccatgaac tgccaactgg ttgtttgacg    2880
agagctactg cagcggtatg aaccgcaccg ggtctgccgg aggccgtttc gtttaagtta    2940
tgcggccatg gctggttcgt ccagcatggc gtaataccgg tcctcggctt cggctggcgg    3000
tatattcccg ataggctcga gaagccttcg atgattgaac caatcgaccc attccaaggt    3060
ggcgaattcc accgcctcga agctgcgcca tggtccacgc cgatgaatga cttcggcctt    3120
gtagagtccg ttgatcgtct cagcgagggc gttgtcgtaa ctgtcgccga cgcttccgac    3180
agacggctcg atgccagctt ctgccaatcg ctcggaatac cgtaagccca cggtgaaggc    3240
cgtcttgcga tgacggcctt ctgactgcca gtcctagtgg taacactagg agtagtcata    3300
tgacgaagca tgcaattgag gtgatcacgt ccgtagagcg ccgtcggcgc tggtcacgag    3360
aagacaaaga gcgcctggtc gctgcctgct ttgagccaga cgcggtcatc tccgagattg    3420
cccgcgcggc tggtatccat gtcagccagt tgtttcgttg gcgcaaagag ctgtgccggc    3480
tcgacgagcc gcagaccgag acgggaaccg tgttcgtgcc ggtgatcgtg tccgaggcca    3540
tttcatcagt ctctcccatt cagccgggag cgccgaccac accccatcct cgtcggaagc    3600
gcagcgatgt gacaatcgag cttggacggg gtcggcgcgt gcgcgtggat agcgacatcg    3660
ataccgaggc gctcggccgc atactcgact gtgtgctggg gctgcgatga tcccggttcc    3720
tgttggcgtg aaggtctggc tggccacggg ctatacggac atgcgcaagg gcttccccgg    3780
tctgtctttg atggtgcagg aggcgctgaa gcgtgacccg atgtgtggac acctgttcgt    3840
attccgcggc gcggcggtg gcctgatcaa ggtgatctgg catgacggcc aaggcgcttg    3900
cctgttcacg aagaagctgg agcgtggccg cttcatctgg ccatctgcgg ccgatggcac    3960
ggtggtgatc acacctgcgc agctcggtta tctgctggaa ggtatcgact ggcggatgcc    4020
gcaaaagacc tggcggccga cgtcggccgg atgagcaaaa acactggaat gatggggtca    4080
aatatgattc catcctgtca tgagcgacgc gaccgaagag cttccggacg accttgccag    4140
tgccctcgca ttgctggccc aggaacgcgc tcgacgtgtt gcagccgaag cagaagcggc    4200
aaccgccaag gcagaagccg ccagtgcaaa ggcactcgta tcgcattccg aagcgctgat    4260
cgctcggctg aagctggaga tcgacaaggt tcgccgtgaa ctctacggca gccggtccga    4320
gcgtaaggcg cggctcctgg agcagatgga actgcaactc gaggaattgg aagcggacgc    4380
cggtgaagat gaactggccg cggagatcgc agccaaagct tcaaccgtca aagccttcga    4440
gcgcaggcgt ccgtcacgca agcccttttcc cgaacatctg ccacgcgagc gcatcgtcat    4500
cgccgctccc gccaattgcg cctgctgcgg atcggccaaa ttgtcgaagc ttggcgagga    4560
catcaccgag accctggagg tcatcccgcg ccagtggaag gtcatccaga cggtacggga    4620
gaagtttacc tgtcgcgagt gcgagaagat cacgcagcca ccagcaccct tccatgtaac    4680
```

```
gccacgcggc tttgccgggc caaacctgct ggcgatgatc ctgttcgaga agtttgccca    4740
gcaccagccg ctcaatcgtc aaagcgaacg ctatgctcgc gagggcgtcg accttagttt    4800
atcgacgctt gcagatcagg tcggagcttg cgccgcgacg ttgaagccac ttcattctct    4860
gatcgaagcg catgtccttg ccgccgaacg tctgcacggc gacgacacga ccgtgccaat    4920
cctggccaag ggaaagacag atacgggccg catttggacc tatgtccggg atgatcggcc    4980
gttcggaggc ctctcaccgc cggcagccct ttactatgcc tcgcgcgatc gacggcagga    5040
gcatccggaa cgccacctga agaccttcac cggtattctg caggcggacg cctatggcgg    5100
ctacaatccg ctgttcaagg gcgatcgcga tccaaatccg ctaagacagg cgttttgttg    5160
ggcacacgcg cgtcgcaagt tcttcgtgct cgcagacatt aatgcgaacg ccaagcgtgg    5220
aaagaacgcc gcgccgatct cgcctatggc gctcgaagcc gtcaaacgga tcgacggcct    5280
gttcgatatc gagcgggaga tcaacgggct tacggccgat caacgcctgg aacgtcgccg    5340
caaggaaagc ctgccgctcg tcgacagtct gcaggcctgg cttcaaaccg agcgtgcaaa    5400
actgtcgcgc agttctccgg tcgccgaggc gatcgattac atgctcaagc gttgggatgg    5460
cttcacgtca ttcctggagg atggccggat ttgcctcacg aacaacgccg cggagcgagc    5520
cctgcgaggc ttcgcactcg gtaggaagtc ctggctcttc gccggatcag accgcggcgc    5580
ggatcgtgca gccttcatgg ccacgttgat catgacggca aagctcaacg acatcgatcc    5640
gcaggcgtgg ctggccgacg ttcttgcccg catcgccgac acgccgatta tcaggctgga    5700
gcagttgctt ccgtggaatt ggatgccgcc gaccgtcaac gctcaagctg cctgacctgt    5760
ggtctttacc ggaggcttac ggaataccga atggacacgt attgaacgcc gcgatccgag    5820
tgatgcacga ggccgctgcc atgagcggga cgccgatcat gaagtgcctg ctccagcgca    5880
tcgaggacga agctcgcatg tgctgtccgg cttgcccgcc agccgacgat gcgacgagcg    5940
aagacgtcga tgacaaaggc cacgtagacg aaaccctgcc aggtggcgac atatgtgaaa    6000
tctgaaaccc acagcctgtt tggtgctggg gctttgaact ggcggttcac ccggtcaagc    6060
gggctcggag ccgtcttgtc cgagaacgtc gtgcggatcg gctttccccg aatgatgccc    6120
tgcaggctca ttgacctcat aagcctggcg acactgcagc gggcgacgtc aaagccttca    6180
cgcttcaatt ccgccagac cttgcgaacg ccatagacgc ggaagttctg ttcgaagaga    6240
cgccgtatct cgatcttcag gccgatatcg ctgcgggcgc ggatcgacag gcgatccacg    6300
tccagacgtt tggcgacatt ctcgtagtag gttgacgggg cgatcggcag cagtctgcag    6360
atcggctcga ccccgaacac accacggtgt tcgtcgatga acgaaatcat cgcttgaagg    6420
ggcggtcgag ctccgccatg gcgaaatagg ccgaagcttt gcgcaaaatc tcgttggcct    6480
gacgaagctc acggttctcc cgctcgagag ccttcatctt ctcggcgaca tcgctcggca    6540
ggcctgctct tttgccacta tcgacctcgg tcttcttgac ccattcgtgc agcgtggctg    6600
gcgagcagcc aatcttggcg gcgatagatg aaacggcagc ccagcgggat ggatgctcgg    6660
cttcgtggtc cagcaccata cggatggcac gggtgcggac ttcaggtgaa aacttgttcg    6720
ttgtcttgct catggtggct ccactttctc agaaattgga gcctccggca aaccccggcgc    6780 ggttcacctc ggccttgtag agaccgttga tcgtttcggc gagggcattg tcataactgt    6840
cgccgacact tccgacagac ggctcgatgc tagcttctgc cagccgctcg gaataccgga    6900
tggacacgta ttgaacgccc ctgtccgaat ggtgcacaag cccgccgccc tgaaccggac    6960
gccgatcatg aagtgcctgt tcaagggcat cgaggacaac ccggtgcggt tcagtatgac    7020
```

```
gctttggcca gccgtgtggg agctcgcttc gcttaacagg cagaccatca actttgcggc    7080
tgaaataacg gttcggtcct catagtggcg tccaataacg gagatgccta caggcattcc    7140
ataactgcct tgccaacgat caaggcaccc gcaccgcgga gtatatcgac acatgctgaa    7200
tccgtgcctc gagaaacacc cttgtatcta ggcgtgccgc atcccgtcgg catgcctttc    7260
gtcgcgatga tgtcttttaac cgcgatggtg acacccttca gcggaccgcc acgtgtcccc    7320
gcgtccagct ctgctgcctg ctgccgaaga aggtacggtt caaagaactc catcgcttga    7380
ggctcaggct ctccagccat gattgctgca attgttgcct cggcgatatc ggaagcggtg    7440
cgagtgcccg actctacata cttcgcgata ctcgtcgccg tcatgtcgtc gggcatggtg    7500
tctcgttcgt ggaacatctt ggcttttcaaa ttagagaaag tgcccccgaa gacgcgaatg    7560 gatcggggggc ggatttgtta agtcagccga tataggcgct gtcgagtgcc atgccgacct    7620
ggtgcaacat ctgcgcttta ccatttgagg acactccgat gcggcaagaa tgtatgccat    7680
gagcgagccg tgaagtgcgc cttagtgcgc cacgtgccgc acctcttttc ttatcaggcg    7740
cttagctgaa aaaggttcga tgactctgtt cgttccgcca tgcacaatca gatcggtcat    7800
aatagctccc aggacaggaa caagctgaaa gccgtggccg gaatatccga aggagtggaa    7860
aacgccgctg gcattgggcg acgggcctat gatgggcagg tgatccgctg tcatggcttc    7920
catgccagcc catgtccgca cgatacgcaa ttgccccacg atgggaaaca gatctgtcgc    7980
ggcacgggca ccctttgaga gctctttgaa gttgacgaag cttcgctggg cgtcgagatc    8040
cgctcttccc tgaagccccc caccgatgac aagcgtcccc tggtccgact gcttgaagga    8100
aagcgggcgc cccacaacgc tgacgaccgg cttcaacaga ggcgcaatgc gttccgtgac    8160
gatcatcatc gaggctttgt ggccgatctg aatgtcatcg ccgaccatgg cggcgatttt    8220
aaccgcccag gctccggcgg cgttgacgac ggttggcgcg atgaattcca tcgtctccgt    8280
cctgacgcgc cagtcggcgc ccgcgtgctc gatcgcgatg acacccgcgc cttcgtaaat    8340
tgtgacgccg gcggcttctg tcgcctggcg gaaagccttg agcgtacggt ggggatctgc    8400
ggcaccatcg tttcgagcga tcagtgcgcc catgcaatgt ggcgagatgg aaggaacaag    8460
gcgcagaagc tccgcgcggt cgatcagttc ctcatggtcg taacccgccg atcgaatctt    8520
ggcgagacgc ttctccagaa cggtgagatg ctcgggcttt ccgcgatgc tcatctgccc    8580 gtaagcatgg aaaccgcaac tgtcgccgac aatgcgctca atgttatgcc acatgtccat    8640
ggcctcgagc gagatcggga tctccgcgag atcgcggttc aatgttctga cgcccgcagc    8700
cgtcgccccg gaagaatgac ggccgaccca agaacgctcc aggatcgcaa ccgttttgcc    8760
agctcgtgcc aggttcatcg cagcagaaag accgtgcaat ccccgccga tgacaatcgt    8820 gtccaatgca ttcccgctca tgacgatctt tcctgactgt cgagggctgc aagttcgctc    8880
aacgtgactg gcttcaatgg cggacgcaca cgatagaggc caacatccgg ggcggcccga    8940
ccttccgcat ccgcaagaac acgcgcaatg gtgtacccgc attgacggcc ctgacaggga    9000
cccatcccgg cacgggtgaa ggctttgatc tgattaggac ccggccgacc cgatgtaagt    9060
tgggcgcgca cggatgcgac acttacttcc tcgcaccgac aagcgatcgt atggtcgggt    9120
ggaacgaata tcgatgggcg ggggcgatac agcttgtcca ggaacgggcg ggttgcaagg    9180
gcctgcctaa ggcgtttgcg tgtcggttcc gcctgaaggg tggcttctag ctgtgacact    9240
cgtccggact tgaatacaat ttgcagaccc gtcagcacgc cgcgcaggca tgccgccttt    9300
gctccgccga tccggccccc atctccggcg acaaagatat tcgcctcgga cgtttcgccc    9360
caactgtcga gctcgggcgc gaagctgtcc tgatcggcgt tccagacgtg tcggcagccc    9420
```

```
aaagcgaggg  tcggatggat  tgtcgggaca  atgccttcat  gaacgagtaa  aagcttcgcg   9480
tcgacagtgg  cggactggcc  gctcgccgtc  acgtagcgaa  ggcgctcaag  gctttccttg   9540
cccgtcgctt  cgatctcggc  cacgtgctgg  atatactgaa  ctcgccgttt  gatcgactgg   9600
agccagccga  ctcccttgag  gatatccatt  ggcgcacttt  tcaacgcgga  aaagagatcg   9660
ggcagcgcgc  tgctgatctg  gcctgcacga  gacgtgtcga  ggaaacccgc  aatccgaccg   9720
cccgctttaa  gaagctgagc  tgcataaagg  agtgagagag  ggccactccc  tgctatccag   9780
accggctcag  atgggatttg  atctgacgtc  ttcagcacga  tctgggcagc  gccgattgtc   9840
atcacacccg  gcaacgtcca  gcccggaaat  ggtgccggcc  tttcctgcgc  acccgttgcc   9900
agaaggaggt  agttcgcctc  gatagagctt  gcggcaccat  cgcgcgtgac  ataggcccgc   9960
gggccggctt  cgacctgcca  tacctgcgtg  cctggttcgt  aacgagcgct  gctggcgcgg  10020
aattgccgga  cgagatcaag  cccttccgcg  taggccttgc  cgaggatgtc  catccgcggt  10080
gtacccgaaa  ccgcttcgat  attacgccag  atctggccgc  ccggggtagg  ctgttcgtcg  10140
acaaccagca  catccagtcc  gtagcgcctc  gccacgaccg  ctgccgacat  acctgcaggc  10200
ccggcgccga  caatgagcag  atcaacctga  cggctcataa  tgcaatcctc  cgccgtccga  10260
gttgccgctc  aatcctcatt  ccatcgcgaa  ccgagacaag  acaggtttgg  acagatgcac  10320
cgtctaccac  ggcaaggcac  tcgaagcaga  ctcccatcat  gcagtaaggt  gcgcgcttgg  10380
tttcggaaac  tggggtcgtg  cgtgaccaga  caggatcctg  acgcaaaaga  actgcggcga  10440
cactttcatt  ggcctcggct  gcgactgcct  caccatcgat  gtagaccgtg  atggctccct  10500
ggggcacttt  attgagtttc  ttgaacatta  gctaacctgc  gcaaccgatc  tgagctcgtg  10560
ggcattaaga  ggaaacccgg  tgacaactcg  ctcaagaaga  ttttcgcgca  tcagcggtcc  10620
gagctcttcg  aggatatcgt  tgccacgacc  gaaatctcgg  tcataacaag  cgctgatgat  10680
gttcacgccg  ctcctgtgaa  ggggcgcggt  tatgccggcg  agctcggcaa  gcaagagcgt  10740
cggcatcagg  ccgaagggta  catcttcaag  gatgtaccgt  gtatcaaggc  tcttcgggcc  10800
catcgggtcg  tttccgcgag  caatgacggc  aaccgccaat  tcccagacac  gatcaccctc  10860
gactttgtgg  gttagcctgt  agtgatcgaa  cacggtgcgg  acatccttcc  cgaacgcgga  10920
ggcgatcgct  acgcgctcac  ggtcgagcgc  ctcgattagg  ttcccaaccg  ccgatgtgag  10980
gttcgtattc  tggccccagg  actcgccacg  ctcgatcctc  gtcagattgc  atagagcaac  11040
ggcgaggtgg  ttctgcggat  tcagattgct  taatgcgatc  gtgagaatgt  catctttgag  11100
gttgaaccgg  tcaccgaaga  cgttcgcgca  tatcgccagt  cccgcgtctg  cgaaacgagt  11160
tggaaccgtt  gccatatcga  ctttgtcccg  gatggtcccg  atgttgaatg  tgttggggcc  11220
gcgttgcttg  ctggtcagca  ccgtcgtact  ccaggccacg  atcgggattt  cgatgccacg  11280
ttcggaaaga  cgctttgaga  gaaacaatgc  ggcaagggac  aggtggctac  tgatgatgac  11340
cgtgtggttc  ttgcggatga  acggtatgag  tgcttggagc  acggatcggt  ggccgtaggc  11400
cggcaacgcc  aatactatga  catcgtttga  agccagctct  tcggctgaac  ggcagatcgc  11460
tggactgaac  tcgccttcga  tcataccggt  gatcgttagg  gcggctccct  tggcgaggtc  11520
caccgttccg  gcccccgtgg  gagaccagac  gcttgctgag  tgaccttgct  tatccagaaa  11580
ggccacgtag  cccatcgcga  ttgctccggc  acctgcaatt  cctacgcgca  tatctcacta  11640
tccttgccac  tatatgtagc  cgttatgtat  ttccaatcat  ttgaaacaga  tcgaaggtcg  11700
cggaggtttg  accgcgatca  tcgcaattcc  cggtttactc  gacttgcacg  acatgtccgg  11760
```

-continued

```
gagaaacctc gacatacttc cgctgcggag gcacgtagtc gatcgaacga acagggctct    11820
tgatttcgtc catctgactg tttctcttga tccggcgcct tgccggatcc ggcacaggca    11880
ccgcggacat gagcttcctg gtataagcgt gctgagggtt gtcgaacaca gctgctcgcg    11940
gcccgatttc aacgatttcg ccagatacat gacagcgac gcggtgactg actcgttcga    12000
cgactgccat gtcgtgcgag atgaacagga atgccaggtt cagactttgc tgcaagtcga    12060
ggagaaggtt acagacctgc gccttaatcg agacgtcgag cgctgaaacg gcttcgtcgg    12120
cgacaatcac cttcgggtcg agcataaggg cgcgcgcgat cgccacacgt tgcctttgcc    12180
cgcctgagaa ctcgtgtgga tagcgcttca tcatttcggc cgagagaccg accttctcca    12240
gaagggcggc ggttttgtcg cgtgcctgcg ccttgcttcc gagaccatgt tggatgaacg    12300
gctccataac tgcatcgccg atattcatgc gcgggttgag cgatgcgtaa ggatcctgaa    12360
aaatcacctg aatcgactga cgaaccttgc gcagtgttcg ttggtcaagc ttcagcatat    12420
catgaccatc gacagtaatg cttccgcttg tcggatcggt aagacgggtg atcgagcgtc    12480
ccgtcgtcga cttcccgcat ccagattccc cgaccaacga caaggtctct ccctcgtaga    12540
ggttgaacga tacctttcg acggcatgca ctgcaccggt cgttcggccg aatattcctg    12600
aacgaattcc gaaccgagtg atgaggttct tcacctcaac aattggcgcc ctgtccttcg    12660
ccaccgtatc ccagacgtcc gcgagaggtt taattcgcc gctttccggg tcgacgatgg    12720
gaaaacgcag aggcaggtgg cttttttccca ttgcccaag cctgggcacc gcggcaagca    12780
gggcacgggt gtagggatgc ttgccgcgat ggaagatttc ttcggtcgga ccggtttcca    12840
cctggtcgcc acgatacatc acgatcgtcc gatcagcgat ctccgcaacc actcccatgt    12900
catgggtgat gaaaagtacc gacattccct cctcatcctg aagctcctta atcaggtcga    12960
ggatctgccc ctgaattgtt acatcgagcg ctgtcgtcgg ttcgtctgcg atcagcagct    13020
tgggccgcga tgcaagcgcc atggcgatca taacgcgctg acgcatgccg ccggagaact    13080 gatgggata ttcgtcgaag cgtcccttcg cgttcggaac gcgcactttg tctaggaggc    13140
caagaacctt ccgcttcgct tcctcagcgg agatgttctg atgaacggtc agggcttcgg    13200
caatttgctt tccaaccggc aagattgggt tgagcgaggt catcggttcc tggaaaatca    13260
ttgagatctc gttgccgcgt acctgtcgca tctcttcttc cgaaagagaa agaagctccc    13320
tgccggcaag gattacacgg ccttcgattc tgctcgaggc ttccgtcagc aggcgcatga    13380
tcgacagcga ggtgacggac ttgcccgatc cagactcgcc gacgatggcg acggtctcct    13440
tgggggcgat atcaaacgag atatcgcgca ccaccgggtt ccatccatct ccagcgcgaa    13500
aggaggtggt gagatttctg accgacagga cgggcgcggc agaagagcct gcatgattga    13560
tttgatcggc gatctggttc atcgctcatt cctcgttttc ggatcgatcg catcgcgcaa    13620
ggcatcaccc agcaaattca gcgcgaggac cgtgagaagg attgcaaggg aggggaagac    13680
aacgagccac caggcgctga ggatgttttc gaatccctcg cggatcattg cgccccaggt    13740
tgccgtgggg ggagcgacac cgagaccgat aaaggcaaga gacgcctcgg tacgaatagc    13800
ggatgccatc cagagcgatg ccacgacgac aatgtcggac aggatgttcg gaaggatgtg    13860
gacgcccatg attctgatcg gcgtgaagcc gagggacttg ctagcgtcga tgaaatcgcg    13920
tcgcttgacg gcaattgtgg gtccgcgtgc gacgcgggca aagggagccg tctcggtgat    13980
cgcaattgca ataataagat tctcaaagct ggcgccgagc attgccgcga ccatgagccc    14040
aaggagcagt gtcgggaacg acagcatgac gtccacaagg cccatgacga tctgatcgaa    14100
gagaccgccg atataacccg cgagaattcc gagcgccgaa ccgacgacca tcgcaatcat    14160
```

-continued

```
cacggaaagg aagccaatcg cgagtgagat acgggcccca tagagcaggc gcgacgccac    14220
gtcgcgaccg aaactgtcgg ttcccagcca aaactgcgcg gatggtgcgc tcaggcggtg    14280
aacgatgttt tgcttcagtg gatcgtaagg tgcgatcatc ggagcaaaaa cggcagccag    14340
cacgatcagg agaagcagtc cgatgccaac ccaggagagg cggttgcgac ggagtgcggt    14400
aagcaccgga tttggcgcct tctcaggctt tgcggattgc aagatgatat cggtcatttc    14460
gcgtaactca ctcttgggtc gacagcggcg tagattacgt cggtcaagat gttgacgagg    14520
accacgaagg ttgcaaacac gaccatcagg ccctgcagca tggtgtagtc gcgtgactga    14580
agtgctccga gaatgagctt gcccagacca ggtcgggtga agacgatttc gacaagaacc    14640
gagtttccga tcatcgtccc gaagttcagc ccgaccaccg tcacgatcgg gataagagcg    14700
ttgccaaggg cgtgccggat gatgatgctc ttggtcttga cgcctttggc gcgcgcggtg    14760
cggatatagt cctcacccaa aacgtcaagc attgaggagc gggtgacgcg ggcgatatag    14820
gcggtcatga tcaggccgag attgagagcc ggcaaagcca ggcttcgcag atgatcaatc    14880
ggattggccg taggccggct catcaccggg aaccaatgca gccagacagc aaatgcgagg    14940
agcatcagaa ttgccgagac gaacccggga acgagaggc cgacgagtga aagaagacgg    15000
cttgcatagt ccggccattt gttgcggcga atagctgcga caatgccaag ggggataccg    15060
aatgccacac cgatgatcat cgcggcggcg gtgagttcga gagtataagg taagacaaca    15120
gcgacttcgg acagtaccgt acggccgctg acggcggaga gcccgaaatt accggtcacc    15180
atgtcaccca tgaagcggag gtattgaacg ggtaacggct ggtcgaggcc gagctgcgcg    15240
cgcagtgcgg cgagcgcttc ggcactggcg cgatccccaa gcattgcgac ggcggcatca    15300
ccgggcacca gccgaacgag gatgaaaacc accgtcagca ttgcgagcaa agtcggtatg    15360
gccaaaagga gtcttcggat tacataggtt gtcatatggt agcccttcca gcatcgatgc    15420
agctcaccaa ctcttcgtca aggttttggg aaattggacc cgcgtcgatc gaagaatcgc    15480
gacgcttggt cgacgagggg aacaatcgga gatctagccc ggaaagacgc ggtataggc    15540 acgcgaaggc tgggcttggc ctcgtccgac cgatacgtct gaaattcagc gaatgagatg    15600
acatattggc gacggccaac acgcgccacc cagagtccca ggtgcgtggg cggccaatgg    15660
tcgggtgatg acatcgcgat attattgcga cctcaccgac gcctgtttca ggcgggaaaa    15720
gttcgataga cacggcggta gttccccata ttattattgt aacttcaaac ccgcaggggt    15780
agaaagtcaa agtcgaaaaa tttggcttca tattcgcgtg ggttatagtt catgagaaat    15840
ccgagccttc ggcaactcga aggtttaata gcggttgttg aaaccgggac tgtgagccgt    15900
gcatcggagg tcctgcggat ttcccagccc gcggccagca agctgatcca ggacctggag    15960
ttggacagtg gtttgaagct gttcgagaga gagagcgggc ggcttgtccc gacgggtcgt    16020
ggaatgcggc tctacgagga aatcaagcgc atctttggtg gtgtcaatca ggtcgcccgc    16080
gccgttgaag cgatgcggag agaggaatct ggccatctcg tgatcggcgt gatgccgagc    16140
ctgtcgggtc cttttctcgg tcgggtcgtc gcgggtttta gatcccgcta tccggacgta    16200
ttcgtggaaa tcgagacgca agcgtctcag tttctgacgg aatcggttct tctgggacgt    16260
attgatctcg cgctggtcaa gagtggactg gagcatccga cgatcattgt tgaacccata    16320
gacagcccgc ccatggcggc agttttgccg ttaggccacc acttgctgga aaagtctgag    16380
ctcagcccgt tggaacttgc ctcagagccc ttcgtcgcgt tcggcgactc aagccgaacg    16440
cgcataaaag tcgatgcggc attcgaggcg cacggcttga agccaaaaat taccatggaa    16500
```

```
gcagcgacag cgccgaatgt cgcggaattc attgctgctg ggctgggcgt tacggtgtcg    16560
gatccgattt cgatggaatg cgtcaaggga cgcgttgcat tgcgtccgtt tctcccaagc    16620
attgatgccg agtacaggct ttatcgcccg gcacgagccc ggcacacgga tctggtgctg    16680
gaattttctc gagaggtgca tctggccgca gccaacacca cacttgccat ctagagcaag    16740
accccggcca gcaactctcc aagaggagga aacgtaggcc ggggcaaggt ggggaggatt    16800
gagacgggct actgcttgaa cgtcgtgttt tccgtgatcg gcggcgccag attcaacgcg    16860
ccttcgagtt cgtacccata gtcaagctcg ttcttacgaa cccagacctg catcaggttg    16920
aaaagcggga ttccgcagac ctgatcatag atcttgtgct gcgcgtccga ccaagccttc    16980
aaacgttcag gatcggttgc agccttgcgg cctgcttcga tctccgaatc ggcggcatcg    17040
caatgcgaga aattggtgac tgccgtcggc tttccgatcg aggcattgga atggtagaac    17100
tggctgagat agctgtcggc aacgggataa cgcgcggcac catagaagac gacgtcgctg    17160
agatccttgc ggctctgttc ctgataggtt gcgtgatcga ccacctgcat gtccatatta    17220
atgccgacct ccgacaactg gccctgcacg acctgcatga tcggctgctg cgcggtggcc    17280
gatgagacga tggccttgat cgtcaagccg ttgcccaaac cggcttccgt gagaagcttc    17340
ctggataatt ccgatcgta cttatagctc caggtgcagt cttcaccaag aaacccgat     17400 gggacgaccg agcaacccct ctgtccgacg cccgccccga cgaattcaac gatctgatcg    17460
acgttcacag catgtgctat tgcctgacgc actttgacgt tatcgagggg cttgtgagcc    17520
tgattaagga acagcgtgcg atattcgccc ggtgcgaaga tatcgaccgt gaaccatcc     17580 catgccttgg cctggtcgac ccagcgctgc tcgcgcttgc cgtatataag atcgagctca    17640
ccggagcgga acgcaagttc gcggctcgcg tccgagggaa tgagattgta ctggatgccg    17700
tccagtttcg gcttgccgcg gaaatagtcc gggaaagcct tcagcgttac cgattgctgc    17760
gtgaccgcgt tctcgaacat gaaaggcccg gttccgatcg gacggagttt gaagtcggct    17820
cccagcttct cagctgcctt tttgctgatg atattgccgc catggtagtt tgcgatcagg    17880
cccaggaagc ctggaaccgg gctgttcaag gtgatcttca cggtcagcgg gtcgatcgct    17940
tcgatcgatt tgacttcggt gaagtcgttc gaaaaagatg acgttttcgg attctttgca    18000
cgctccaggg agtagacgac gtcctcggac gtcaccgtgc cgtagtcacc gtgaaacttg    18060
acgccatttc tcagatggaa agtccagacc agaccgtccg gcgtagtttc ccacttttcg    18120
gcaagatccg gctcgatctt tgtcgggtcc gcgctgccgg gcgggaagcg aacaaggccg    18180
ttgaacatcc atgagacgac accgacatcg acggtggcgg tggccctggt cggatcaagc    18240
gtggcgacgt tttcggcggc agcaccgacg cgtagcgtgg ctgcctctgc ggcacacgga    18300
agtgcagctg tcgacagaaa aattgcgatt agcgcggaaa ggttcaattt cccagtgtga    18360
gatatcatgt tcgcctcctt tgttattgtt tccactaaat ttcaaaggcg tataagtgtc    18420
aaagtcgctg atttgggcgt ggtattcgca cgggttatat ttaccctcca cggtgtgtgc    18480
aattattcaa ccgtgagctt tccagttggc actgctgttg gagcaagact gagaaaagcc    18540
ggaagtcgtt gatttcgaga tgtttgtcga gtgtaggttc tccggttttg cgcgcaatta    18600
tcatcgtcgg cctttcattg atctcaagga aatcttgacg cacagggcat ggtgcgctga    18660
tcgccgacgg atcctctctc tctctctctc tctctctctc tcctgcctct cagatgctga    18720
accatgctcg caaacgaatg ggctgagccg ataagagtgc ccgcctttt ggaggcaccc     18780 cgaattgctt gctaggctgc gatttgccgg gcttcccatt catgtcgcag atcatgaccg    18840
caatgaccta gcaagacctc gctatattgc cagaccggtg gcttcaagtc cgccggacgg    18900
```

```
atcggactttt tgagctcgtc attcgaggcc gggcgaatct aataacgcg tgccgggtca    18960 gcaaccggga cggcagatag aaggcgtttg gtttagggta ttgtacgttc tcgaaaattg   19020
cctgccgcgg ttctatctcg acaatctcgc caagatacat caccagaacg cggtggctta   19080
cgcgttcgac ggctgcagtg tcatctgaaa caaagacatg gtgatggaag ctgtcgtttc   19140
cggtcgggcc gacataggct acgcggatgg cccctcagat cgccccggct ttcttttgga   19200
aacccgctcg cttgccgcaa tcgtcgctat acggatggga cacaggctgg ccggtctcga   19260
gcggattacc cctcaggatt tggctggcaa acggatcata aaacaggaaa caggcacact   19320
gttcgccatg cgggtcgagg tggccattgg cggtatcccc cgtcgtccct ttcctcgaag   19380
tgaacttgtc gcatgcggca ttcagtctgg tccgcgaggg cgcggggatc gcaataatcg   19440
atcctgccgc agccatcgaa ttcaaagaca ggatcgtgct gcggccattc tcgatattta   19500
tcgatgcggg gttcctcgaa gtccgttcag tgaacggtgc tacctctata atcgtggatc   19560
gtttcgcaac tgaattttgg aactttcatg acgccttgat ggcacaaagc tgtttggtaa   19620
gctgacctgt tctagcacta ctttggcgaa aaggttcgaa tgtgtggaac atgtccgtcg   19680
acgtgaattc ttccagactt cgaggggctg aagcccgcca ggagtgttgc gttactcagc   19740
aagtaagtac ggagaagcaa ggggtcactt tgtctttctt ggagcgatca agcatctgac   19800
ggattattat cggcctacct atcatcccca cgtgttggct gcccgtggcg atctgggcat   19860
cacgctgccg atctcaggga caggctacgc gctcgaattg atttcctttg tcacattatc   19920
gatgggcttc ttgatctgct gcgtcggctt ggcagtagtc tacggctcga cgccgaacga   19980
acaaagattt tcgttgatga actagatgac tgcttgaaga gtcgggccat cagcaccttc   20040
ctgaaagaag ccgaaacttt gcgcagaatc ttgttgcgtg ggaaagttca cggggctccg   20100
ctcacgagcc ttcgttgtat tagccatatc gatgcggcct tagcatttgc aattgtcgcc   20160
tctctccttc atctactcat gtagcgctac ttacaatcgg aaattggata cgagaaacag   20220
gtaacaggct attgctgcag gcaccgccag accacgacgc cagtcgccgg tccgcagtta   20280
gcgggaatag cgaccgaagg cccgaaacgt ctgcccaaat ctagcccttt tttgctagga   20340 cttttgagaaa aggtccgtgc aaatgttcgt tgatgcgaaa atttgtctat gctcttcctg   20400
tggatgggaa gttggaatgt ccgcgggttt gcaaagtaga aatgtccgca tgtcaccaca   20460
cgcaacaccg accagccccg atctgagcgg ctgatcccgc ttgcaagatc agatcggggc   20520
gggtgattga cacacctctt cggctttagc tttgagacgc ctcactccgc agccggctgt   20580
tgcgacagtg ctttctttcg ccgcgcaatc acaaccggat cggtcgtgaa gtctttccga   20640
cgaccaggtc cacgagcgcg tttgatgtat ccattcttat cgctgttgtt cttcacgtca   20700
ggcgccgggc gctcgtcctg acgctccttg atatatgcca ggacatcacc gagccgcctg   20760
ttctcggtga tcgccgcatg cgttacccgc tggtccttgt cgaacacctg atagggcagg   20820
gaatgtccct tccatcgcac atccagccga ccgtccgcat aggcataggt ctcgacataa   20880
cggccaacca ggccacgcgt caccgcggtc tcctccagca tgatccgctt gcgctcgaac   20940
gaaaacgtca gctgcgatcc gacatagcgc tgctcgcgct tgcacaggat ctcagtcaac   21000
cgatccggcg ccagattcag cggccgatgc agatcgtcgg gacgggcagg gacgattgca   21060
aaacgcgcgt tgtagtcctc tatgaagccc ggcaagaacg cattgcccgc ctgcatgctg   21120
tcgatgccag aaagcctgag ctccttgacc aggcgatcct gcagcgtccg gttcatccgc   21180
tcgacccgac ccttggcctg gctcgaattt gcacagagaa tctcgatgtt tagctcgcag   21240
```

```
agcgcacgcc cgaactgggt catgccctga ccacccctgg catccttctt cgccacccgg    21300
aacactgaat gcttgtccga atagaaggca accggcgcgc catgacgctt gagatacagc    21360
tccaatgcct cgaaatagct gaaggcactt tttcggagcg cacgaagcgc agctgcatca    21420
acctgccggt cgcatcgtcg acaaatacca gcagcgagca agacggtccg cgatcctcga    21480
accagcgatg ctccgagccg tcgatctgca ccagttcgcc ataggcttct cgccgtaacc    21540
gcggctgatg aaacgtccgg cgctgcttgc gcgacagcca ggggccggca tcagtcatcc    21600
agctgcgcac cgtctcgcgc gatacacgca gtccattgcg ctcggccagc ttctccgtcg    21660
ccaatgtcgg cccgaaatcc gcatagcgtt cgcgaaccag cgtcattgca taatcgcgaa    21720
ccccggcgct gatccggttg ttcgacggcc gaccgattgc cttgtgccgg atcgaagccg    21780
ccccgccagt ccgcatgcgc tccagcagcc ggcgcacctg cgctcgctc agatcaagca    21840 catgcgccgc cgataccgtg gtcatccggc cggcaaccac cttcgacaaa atctcgatcc    21900
gttgcagatc gcgctcgctc atcgctatca atcccatctg caatctccca ggcatcgtta    21960
aggcccgggg agagtgacat tccaactttg aagaatcagg acacttcaac tttgcggcta    22020
cacttcctgt cgacgtaata tcgattatga gatagcgttt ccagccgct tcacgttcgg     22080 tgcaatgtag tttcaaatca tacgcgttaa ttttcactga tggggttggag gagcaactgg    22140 tcgttgccag accgcgccga cggcgttttcg gatcatacct ggggaaaaat aagtccggca    22200
ccgagaacct aatcaatcgc gatttccatg caaaagcgcc gaacctgaag tggctgacag    22260
atatcaccgg gttcaatatc ccagccggga acgtctacct tgcgcgcatc atcgactact    22320
tcgacggaac ggtcatcagt tggtcgattg gatcgcaacc agacgcgggg gaatactatg    22380
cttgatgcag ccattgagac catgacagac ggcgaggaac gaccaatcgt ccattccgct    22440
cgcggagctc attatcgctg gtcggctgg ctaatgcgga ttagcgaagc aaacctaatt      22500
cgctcaatgc cccgaaggac tgctcacaag ataactttgc ttgtgaggtc ttcttctgcc    22560
ggatgaaaac agagctcttc tatccccgag actggaaggc tattagaatc gaacagttcg    22620
ttgccgagat agacgcttat atccgctggt acaatgagag gcgtattaag atatccctgg    22680
gatcactcag cccgatcgaa tatcgaagaa gtcttggccc taacttgtaa agctgtccaa    22740
ctttttatcc acacccccctc cgggtcagtt ctcaatggc                           22779
```

<210> SEQ ID NO 3
<211> LENGTH: 4993
<212> TYPE: DNA
<213> ORGANISM: Agrobacterium tumefaciens

<400> SEQUENCE: 3

```
gcgtaagacc agtcgcagaa gttttatgat gggcgccggg gcgatagctc tcgcgtcaac       60
cgcaggcgga aattttgcat ctgccgcgga tcgtcgcgcg ttgcgcatcg gtgtaaatgg      120
gctacctccg tcgctggagc cgatcaacgc cattagcaac accggcccgc gtatcatcaa     180
ccagattttt gatgccttga tccggcgcga ctattttgcg gatggtgcca aaggcaacaa    240
tatcaagctt gtgccggcac tcgctgaaag cttcgaacgg attgacgaca agtccatccg    300
gttcaagctt cggcaaggcg tcaaatttca aacggcgcc gagatgacgg cggaagatgt     360
tgcgttcacc ttctcttctg agcggctgtg gggtgacgaa gcgatcaaga cggttccgaa    420
tggccgaaat ttttctccca actgggacga gccggtcgtg aagacaagt acaccgtcgt     480 tttgcgtacc aagacgccgt cctatctcat cgagaaatat ctcggctcct ggctcggcc    540 gatcgtcccg aaggagtatt acaagagcct cggtgcagtt gccttcggta acaagccgat    600
```

```
cggcacaggg ccatacaagt tcagggagct tgtcgctaac gatcatgtga cgttggaagc    660
gaatgacggt tactggggcg ataagcctac ggcctcgaca atcacttacc aggtcgtagc    720
ggagccagcc acgcgcgtgg ccggtctgat cagtggtgag tatgacatca tcacgacgtt    780
gacgccggac gacatggcgt tggttgacgg ctactctgac ctcgaaacgc gtggcacgct    840
gatcgagaac ctccatatgt tcacgttcaa catgaaccag ccaatcttcc agaacaagac    900
tttgcgtcgt gctctggcgc ttgctgtcaa tcggccgctt atcgtcgagg ctttgtggaa    960
gaataaggct tccataccga acggctttaa tttcccgcat tacggcgcga cttacgaccc   1020
gaagcggaag cctatggaat tcaacctcaa agaggccaag cgtcttgtca aggaaagcgg   1080
ttacgacggc accccgatca cctatcatac gatgggcaac tattacgcca acgctgtccc   1140
cgcgttgatg atgatgattg agatgtggaa agccgccggc atcaccgtcg tgccgaagat   1200
ctttgcgccg gggacgacac ccaaggactc cgacattcta atccgcaact ggtcgaacgg   1260
ccagtggctc acggacggcc tcacaacgat ggtatcggaa tttggtcctg ccgcggtgt   1320 ccagaagcgc tggggttgga aggcacctgc agagttcaac aacctctgcg accaggtggc   1380
ccagctgaag gatggcgaag agcgttccgc agccttcaac cgccttcgtg atatcttcga   1440
ggacgaagct cctgctgtcc tgatgtatca gccttacgat gtctacgctg cacgcaaaga   1500
cgtccagtgg agtcctgttt cattcgagac catggaattc cgcggaaacc tcaatttcaa   1560
ataacaacaa tccaacgaga tggcggtgcg catccgtgcg caccgctcag ggaggatgaa   1620
atgtctactt tgttgaatgt tcgtgatctc gtggtcgagg tgccggcccg caatatccgg   1680
attatcgacg gtgtcagttt ctctttggaa gccggccaga cgctggggct cgttggcgag   1740
tctggttgtg gaaaaagcat gacgtgctac gcggtgggca acatgcttcc gcggggaatt   1800
gcgaaaaccg gcggatcaat cgaattcgga gcgaaccgga cggcgtccgc caaatccggc   1860
aagccgacga tcgcgatgat cttttcaggac ccgacaagca gcctgaaccc ggtccacacg   1920
atcggctact acctggagtc cgcccttttac cgccaccagg gtctgaaagg cattgatgct   1980
cggctggaag cgatgcggct tcttgagcgt gtcggtatcg atcgggccaa aagccggctg   2040
cgatcctacc cgcatcaatt ctccggcggc atgaaccagc gcgttatgat cgcccatgct   2100
ctggcagcaa agccccaact tttgatcgcc gacgagccga cgacggcgct cgatgtgacg   2160
atgcaggcac agatccttca tctgctcgaa gaactgaaag ccgagaccgg catggcgctg   2220
attattgtat cccacgatct aggtgttatc gcgcgtctcg ccgatagggc ggcagtgatg   2280
tactgcggaa aaatcgtcga gacggcgccc gttgcggaat tgtttgaaag accggcccat   2340
ccgtatgctc gcgctctgat cgaatgcatg ccgagtatcg aggcggacga tctcgaaccg   2400
ccggtcccga tccccggatc tgtaccgcta ctcgataacc ttccccaggg acccgcagca   2460
acagcgtgtg cacgaccgga acggatgcta ccgcagccca tgacgtggat gccctgcaga   2520
agcggcgaat ggtcttcgtc gccattccac cattccgctg cgcgttccat cgcggccgtg   2580
cgcgatgcga gcgcaacttt ccactccgga acgccaggcc ttactgcatc tcggcttgcc   2640
aggaactggt gtgctgcgat atcgcgcta cggcgaacaa cgtcaatcgt tgcctgatcc   2700
ttacgtcggc gcacctcgcg gatgatgtca gtaatatcga cgattcgatc gcgaccgaga   2760
gcatcgcgaa ccagatccag gctgcgcgcg gaggtggcgt caaaatctac gccaatcttg   2820
cgtgctgttg gggcgaccgc ctcgatatgc tttgccagag cagccgaaaa ggacattggc   2880
gtcttggctg gctcttccca ctcaacccat tcgacggcga ccggaacggt acactgcgag   2940
```

```
cgaatttcag gtgcttcgat gcgtggagaa atgaacgccg ggttgccatc ctgagggaag    3000
acgaaccaga tcggcctcac ggatgcgatg ccgtcgagcc cggtaaagaa gcgatggttg    3060
tcgaagctcg acaatgcgag aacgtcaatg ccgttctcct tcattgcggt tctggcgcgc    3120
tctatgcgcc tggtgtagtc ggcttcgttc ggaaatgtca gtttggagtc tgctgggttt    3180
tctgtcatgg cgctctcaca aggaatatc gcgggtgata ggacgggcgt gaccaaaggc    3240
accgcgcgtc ccgcagatta gcgcagagta ttgggctgcg tctttaccgg cttctacgag    3300
tggaacgccg ttcaatacgc ggcatgccaa tctggcgaca aatgcatcgc ctgccccgag    3360
ggtgtcgacg gcatccacgg gcactgcggg tacgaaaagg gcttcaccct tataggatac    3420
ggtcgcccct ttagctccct gcgtaattgt tacgagctcg actccggcag aatgggcgat    3480
atcgaggacc cgggcgattt cagtctcgct cgcacccgag cgcgagaagg ccgcaacctt    3540
cacgtagggc aatacgctcg ccgcataatc cagatcacga tccgaaaaat cgaaggagat    3600
cgcaacccct tcgcggattt cgggaagctg ccgtctaag cgactcgtct cacccgtatg    3660
agccagatca aacctgcga ggtactcaag ttcagcacta tcgagctgga gcatcgacac    3720
gccctttcg caaggcccc atttccgatt gttgccgtcg tcatccatgt gaacggtcgc    3780
aaaggcattg gggccgtcct tgacacgcag atgtgtcaga tctacgcctt cggcctggag    3840
gctcgaccgg atcagatcac catccgagtc cgtcccgata actccaaggt aggcagcatc    3900
cattccgctg cgcgcggcat ggacggcgaa attcaccgca ttgccaccgg gaaacatcag    3960
ctttgatta taatatcggt cgaccacatt gtcgccgacg ccacaaatac gcatgtcgct    4020
gcctcagtag gttgtttga acatgtagcg gcggtctgtc agcaggtgcc cggtgacagc    4080
ttgataatgc tcggcgaggc gcttcgagag cgtggacaga agcagtggag aaatctcacc    4140
gcgcattgac gcgggtacac ccggcaaggt gtagtcttta gagtcgacga caaggcagcg    4200
cttggtgttc ttgttgagga acgtttcaac acgatcgatc acagcacggg tgtcgtcttc    4260
gcccttgaac agcaggactg gcgtatcagg ctgaacgact tcgaaagcac cgtggagaaa    4320
tcgttcgca ttgaaccagg atgcatgctt ccactgcatt tccatcaggt agcacatcgc    4380
aaacccgtag cccgcacctt gatttggtcc agcggagagg acataggtga atggctcggg    4440
accaaaggtt ttggcgattt catgcagatg agcctctgct tcttggattg ccttctcgaa    4500
agcggccggc acagcggcat aagcctggtc gattgtcgtg aaatcgagtt tagaaccagc    4560
ggccttcaac agcgccgtga ccatcaggcc gatcagaacc tgcttcggag caaggatcgt    4620
gcggtcgctg ttataggtga agaccctcatc gcattcagca gcaaggttgg tggtctcgtt    4680
cttttgtgaag ccaataacgt gagcgccggc ggcgcgcgcc cagcgggcgg cttcgatcgt    4740
ctctccagtc gtgccgttat gggaggcgac caggacaacc gactttggac cgagcaatgc    4800
agggcgacgg cgattaaact cctcgctgtt gaaaatgaac gtcgggaatt cagcagcacg    4860
atctgcaagg tatgatgctg ccagagaaatc gttgtaggag ccaccgcaac caacaaggaa    4920
caggttgctc atgttcttgg ctgctgtctg tgccacgcta gcgatacgtt cacgctgcgc    4980
gaccgccgcc tct                                                        4993
```

<210> SEQ ID NO 4
<211> LENGTH: 23
<212> TYPE: DNA
<213> ORGANISM: Agrobacterium tumefaciens

<400> SEQUENCE: 4
gtctgaccgt cccaccaaag aag                                              23

<210> SEQ ID NO 5
<211> LENGTH: 23
<212> TYPE: DNA
<213> ORGANISM: Agrobacterium tumefaciens

<400> SEQUENCE: 5
gggatccgct tcaacacaag tcc       23

<210> SEQ ID NO 6
<211> LENGTH: 18
<212> TYPE: DNA
<213> ORGANISM: Agrobacterium tumefaciens

<400> SEQUENCE: 6
gccgcgaagg cgagttcc       18

<210> SEQ ID NO 7
<211> LENGTH: 20
<212> TYPE: DNA
<213> ORGANISM: Agrobacterium tumefaciens

<400> SEQUENCE: 7
gctcgaggcc gtaccaactg       20

<210> SEQ ID NO 8
<211> LENGTH: 18
<212> TYPE: DNA
<213> ORGANISM: Agrobacterium tumefaciens

<400> SEQUENCE: 8
cggcatggca ccgtcgag       18

<210> SEQ ID NO 9
<211> LENGTH: 20
<212> TYPE: DNA
<213> ORGANISM: Agrobacterium tumefaciens

<400> SEQUENCE: 9
gtgcatcgct ggtgggcaag       20

<210> SEQ ID NO 10
<211> LENGTH: 22
<212> TYPE: DNA
<213> ORGANISM: Agrobacterium tumefaciens

<400> SEQUENCE: 10
catgcggtag ttgacgatac gg       22

<210> SEQ ID NO 11
<211> LENGTH: 23
<212> TYPE: DNA
<213> ORGANISM: Agrobacterium tumefaciens

<400> SEQUENCE: 11
atccagctca agtcgcatcc aac       23

<210> SEQ ID NO 12
<211> LENGTH: 25
<212> TYPE: DNA
<213> ORGANISM: Agrobacterium tumefaciens

<400> SEQUENCE: 12
ctccgcttac aacaccggta atttc                                          25

<210> SEQ ID NO 13
<211> LENGTH: 19
<212> TYPE: DNA
<213> ORGANISM: Agrobacterium tumefaciens

<400> SEQUENCE: 13
caccgcacaa gcttggggc                                                 19

<210> SEQ ID NO 14
<211> LENGTH: 21
<212> TYPE: DNA
<213> ORGANISM: Agrobacterium tumefaciens

<400> SEQUENCE: 14
ggcaccagat cggcatgatc g                                              21

<210> SEQ ID NO 15
<211> LENGTH: 23
<212> TYPE: DNA
<213> ORGANISM: Agrobacterium tumefaciens

<400> SEQUENCE: 15
caggccaatc caccttcct acc                                             23

<210> SEQ ID NO 16
<211> LENGTH: 27
<212> TYPE: DNA
<213> ORGANISM: Agrobacterium tumefaciens

<400> SEQUENCE: 16
aacatgatgc cgtatgactt tctcttc                                        27

<210> SEQ ID NO 17
<211> LENGTH: 24
<212> TYPE: DNA
<213> ORGANISM: Agrobacterium tumefaciens

<400> SEQUENCE: 17
atgactcagc aacctactat cccg                                           24

<210> SEQ ID NO 18
<211> LENGTH: 29
<212> TYPE: DNA
<213> ORGANISM: Agrobacterium tumefaciens

<400> SEQUENCE: 18
gataaaattg aggtcttcct gtttggagc                                      29

<210> SEQ ID NO 19
<211> LENGTH: 20
<212> TYPE: DNA
<213> ORGANISM: Agrobacterium tumefaciens

<400> SEQUENCE: 19
gcagtgctag agcgttcacg                                                20

<210> SEQ ID NO 20
<211> LENGTH: 20
<212> TYPE: DNA
<213> ORGANISM: Agrobacterium tumefaciens

<400> SEQUENCE: 20
agtggtcttg atgacggcgt                                                20

<210> SEQ ID NO 21
<211> LENGTH: 18
<212> TYPE: DNA
<213> ORGANISM: Agrobacterium tumefaciens

<400> SEQUENCE: 21
gcgtcgggtt ccgccata                                                  18

<210> SEQ ID NO 22
<211> LENGTH: 18
<212> TYPE: DNA
<213> ORGANISM: Agrobacterium tumefaciens

<400> SEQUENCE: 22
caccgggccg cacttttg                                                  18

<210> SEQ ID NO 23
<211> LENGTH: 25
<212> TYPE: DNA
<213> ORGANISM: Agrobacterium tumefaciens

<400> SEQUENCE: 23
gccagagaaa acgaacgtat catta                                          25

<210> SEQ ID NO 24
<211> LENGTH: 24
<212> TYPE: DNA
<213> ORGANISM: Agrobacterium tumefaciens

<400> SEQUENCE: 24
cgacaggtgg gccagtagca ttac                                           24

<210> SEQ ID NO 25
<211> LENGTH: 22
<212> TYPE: DNA
<213> ORGANISM: Agrobacterium tumefaciens

<400> SEQUENCE: 25
cgccggtctt gtagattcga gc                                             22

<210> SEQ ID NO 26
<211> LENGTH: 19
<212> TYPE: DNA
<213> ORGANISM: Agrobacterium tumefaciens

<400> SEQUENCE: 26
ccatggcgca gcttcgagg                                                 19

<210> SEQ ID NO 27
<211> LENGTH: 23
<212> TYPE: DNA
<213> ORGANISM: Agrobacterium tumefaciens

<400> SEQUENCE: 27
cgcattgatt gcttgggtag agc                                            23

<210> SEQ ID NO 28
<211> LENGTH: 23
<212> TYPE: DNA
<213> ORGANISM: Agrobacterium tumefaciens -continued

<400> SEQUENCE: 28
cgcgaaatga gcgcctaaag ttc                                    23

<210> SEQ ID NO 29
<211> LENGTH: 21
<212> TYPE: DNA
<213> ORGANISM: Agrobacterium tumefaciens

<400> SEQUENCE: 29
gcgggaatag cgaccgaagg c                                      21

<210> SEQ ID NO 30
<211> LENGTH: 21
<212> TYPE: DNA
<213> ORGANISM: Agrobacterium tumefaciens

<400> SEQUENCE: 30
gctggaggag accgcggtga c                                      21

<210> SEQ ID NO 31
<211> LENGTH: 22
<212> TYPE: DNA
<213> ORGANISM: Agrobacterium tumefaciens

<400> SEQUENCE: 31
gcaagccgag atgcagtaag gc                                     22

<210> SEQ ID NO 32
<211> LENGTH: 22
<212> TYPE: DNA
<213> ORGANISM: Agrobacterium tumefaciens

<400> SEQUENCE: 32
cgagaaccgt cggatcgttg gc                                     22

<210> SEQ ID NO 33
<211> LENGTH: 25
<212> TYPE: DNA
<213> ORGANISM: Agrobacterium tumefaciens

<400> SEQUENCE: 33
gatgtactgc ggaaaaatcg tcgag                                  25

<210> SEQ ID NO 34
<211> LENGTH: 22
<212> TYPE: DNA
<213> ORGANISM: Agrobacterium tumefaciens

<400> SEQUENCE: 34
ctttggtcac gcccgtccta tc                                     22

<210> SEQ ID NO 35
<211> LENGTH: 24
<212> TYPE: DNA
<213> ORGANISM: Agrobacterium tumefaciens

<400> SEQUENCE: 35
ggcgagtctg gttgtggaaa aagc                                   24

AGROBACTERIUM TUMEFACIENS STRAINS

PRIORITY CLAIM

This application is a 371 of International Application No. PCT/US20180/043856, filed Jul. 26, 2018, which claims priority under 35 U.S.C. § 119(e) to U.S. Provisional Patent Application Ser. No. 62/541,221, filed Aug. 4, 2017 under 35 U.S.C. § 111(b), the contents of each which are incorporated herein by reference in its entirety.

SEQUENCE LISTING

A Sequence Listing in ASCII text format, submitted under 37 C.F.R. § 1.821, entitled "80562_ST25.txt", 48 kilobytes in size, generated on Jul. 27, 2017 and filed via EFS-Web is provided in lieu of a paper copy. This Sequence Listing is hereby incorporated by reference into the specification for its disclosures.

FIELD OF THE INVENTION

The present invention relates generally to the field of plant biotechnology. More specifically, the present invention relates to *Agrobacterium* strains and cells which have been modified to be useful for transformation of host cells, such as plants or fungi, methods thereof, and to transgenic plant cells produced by such methods.

BACKGROUND OF THE INVENTION

*Agrobacterium tumefaciens* is a gram-negative soil bacteria that causes the crown gall disease in plants by infecting cells through wound sites. *A. tumefaciens* infects by injecting into the cell a strand of DNA (termed T-DNA) derived from the large tumor-inducing (Ti) plasmid (van Larebeke et al., 1975, Nature 255: 742-743). The T-DNA then integrates into a chromosomal location in the plant and produces enzymes that synthesize hormones which cause the crown gall symptoms, including tumor formation (Chilton et al., 1977, Cell 11: 263-271). The genes encoding these enzymes, and the eukaryotic regulatory control elements associated therewith, are located on the T-DNA. In addition, the integrated T-DNA also encodes enzymes that direct the synthesis of compounds known as opines, which are amino acid and sugar derivatives. Exactly which opines are produced varies depending upon the *A. tumefaciens* strain.

Mobilization of the T-DNA requires proteins encoded by genes located elsewhere on the Ti plasmid and on the bacterial chromosome, called collectively the vir genes. vir genes are activated by certain elicitors from wounded plant cells and act within the *A. tumefaciens* cell to synthesize and transfer a single-stranded copy of the T-DNA (the T-strand) to the plant cell (Zambryski, 1992, Ann. Rev. Plant. Physiol. Plant Mol. Biol. 43: 465490; Zupan and Zambryski, 1995, Plant Physiol. 107: 1041-1047). The T-DNA sequence on the Ti plasmid is flanked by short 24-bp imperfect direct repeats (Yadav et al., 1982, Proc. Natl. Acad. Sci. (USA)), which are required for the recognition of the T-DNA (Wang et al., 1984, Cell 38: 455-462). Sequences immediately surrounding these borders appear to be involved in the polarity of T-strand synthesis, which initiates at the right border (Wang et al., 1987, Mol Gen. Genet. 210: 338-346).

The discovery of the mechanism by which *A. tumefaciens* infects plant cells, i.e. by DNA transfer, led to the realization that this microorganism might be useful, via its Ti plasmid, for transferring agronomically useful genes to plants. It is known in the art that foreign DNA flanked by T-DNA border sequences can be transferred into plant cells using *A. tumefaciens* as the vector (Hernalsteens et al., 1980, Nature 287:654-656). Furthermore, inactivation or removal of the native T-DNA genes involved in hormone synthesis renders *A. tumefaciens* incapable of producing the crown gall disease symptoms. This process of inactivating or removing genes responsible for disease symptoms is termed "disarming." Disarmed *Agrobacterium* strains are now routinely used to introduce exogenous DNA into plants by a process referred to as *Agrobacterium*-mediated transformation.

*Agrobacterium* has a diverse dicot host range, and additionally some monocot families. There are several different strains of *Agrobacterium*. A major disadvantage of using *Agrobacterium* for plant transformation is the organism's host specificity, resulting in low levels of transformation in certain plant species and/or genotypes. Soybean (*Glycine max*) has proven to be very difficult to transform withAgrobacterium. This is at least in part because it is refractory to infection by known strains of *A. tumefaciens*. Studies with a number of soybean cultivars and different *Agrobacterium* strains have suggested that soybean susceptibility to *Agrobacterium* is limited, and may be both cultivar- and bacterial strain dependent. One strain, A281, is a supervirulent, broad host-range, L,L-succinamopine-type *A. tumefaciens* with a nopaline-type C58 chromosomal background, containing the L,L-succinamopinetype Ti plasmid, pTiBo542. Disarming this strain has produced EHA101 and EHA105, strains now widely used in conjunction with soybean transformation.

Unfortunately, transformation of soybean using even these strains remains inefficient. There is still a significant need for strains of *Agrobacterium* capable of effectively and efficiently transforming soybean. The *A. tumefaciens* Chry5 strain, which was isolated from naturally occurring galls on *Chrysanthemum morifolium*, has a wide host-range and the ability to produce tumors on multiple plant species including soybean, tobacco, tomato and sunflower (Bush and Pueppke, 1991, Appl Environ Microbiol. 57: 2468-2472). Of particular interest is the high level of virulence of Chry5 on soybean. Its potential for efficient soybean transformation was noted by Bush and Pueppke (1991).

Both the chromosomal background and the Ti plasmid of Chry5, as well as another plasmid present in the Chry5 (the "cryptic plasmid") appear to contribute to its supervirulence on soybean (Kovacs and Pueppke, 1993, Mol Plant Microbe Interact. 6: 601-608). The Ti plasmid of Chry5 is referred to as pTiChry5. A fully disarmed pTiChry5 in the Chry5 strain would potentially retain the supervirulence on soybean without causing crown gall disease symptoms. Such a strain would be extremely useful for transformation of plants, such as soybean, which are known to be difficult to transform by readily available *Agrobacterium*-mediated systems. pTiChry5 has two T-DNA regions, TL-DNA and TR-DNA, which are separated by approximately 15 Kb (Palanichelvam et al., 2000, Mol Plant Microbe Interact 13: 1081-1091). A partially disarmed Chry5 strain KYRT1 (Torisky et al, 1997, Plant Cell Rep. 17: 102-108; U.S. Pat. No. 5,929,306), which still contained an entire TR-DNA and a portion of TL-DNA, exhibited high efficiency in transforming pea (Grant et al., 2003, Plant Cell Rep. 21: 1207-1210) and soybean (Ko et al., 2004, Planta 218: 536-541). However, this strain was not fully disarmed. A fully disarmed *Agrobacterium* strain would be advantageous for production of transgenic plants which satisfy commercial and regulatory requirements. A fully disarmed pTiChry5, named pTiKPSF2, was constructed in *E. coii* and introduced into a C58-derived NTL4 strain by electroporation (Palanichelvam et al., 2000). The resulting strain, NTL4 (pTiKPSF2) successfully transformed sorghum (Howe et al., 2006, Plant Cell Rep. 25: 784-791). However, the resulting strain is not a Chry5 strain. Repeated efforts in several labs to introduce pTiKPSF2 back into the cured Chry5 strain (Chry5C) were unsuccessful. There is no report of another disarmed Chry5 strain. Since both the chromosomal background and pTiChry5 contribute to Chry5 supervirulence and its ability to transform cells, there remains a need in the art for a Chry5 strain carrying a fully disarmed pTiChry5.

SUMMARY OF THE INVENTION

The present invention provides compositions and methods for *Agrobacterium*-mediated transformation. The present invention provides an isolated *Agrobacterium* strain or cell comprising a disarmed pTiChry5 vector, wherein the disarmed pTiChry5 vector comprises a nucleic acid sequence at least 70% identical to SEQ ID NO: 1, SEQ ID NO: 2, or SEQ ID NO: 3. The invention further provides a bacterial cell of the *Agrobacterium* strain. The invention further provides the isolated *Agrobacterium* strain described above, wherein the strain is an *Agrobacterium tumefaciens* Chry5 strain. The invention further provides *A. tumefaciens* strains Chry5d1, Chry5d2, and Chry5d3, wherein representative samples of each strain have been deposited as ATCC Accession Nos. PTA-124251, PTA-124004, and PTA-124005, respectively. Strains Chry5d1. Chry5d2, and Chry5d3 each comprise disarmed variants of the pTiChry5 vector. Strain Chry5d3 comprises a fully disarmed variant of the pTiChry5 vector. The invention also provides strain Chry5d2 which comprises a disarmed pTiChry5 vector, wherein the nucleic acid sequence of said vector is SEQ ID NO: 1. The invention also provides strain Chry5d3 which comprises a fully disarmed pTiChry5 vector, wherein the nucleic acid sequence of said vector is SEQ ID NO: 2. The invention also provides strain Chry5d1 which comprises a disarmed pTiChry5 vector, wherein the sequence of said vector is SEQ ID NO: 3. The invention further provides isolated strains and bacterial cells thereof.

The invention also provides variant or mutant strains or bacterial cells of Chry5d1. Chry5d2, or Chry5d3, wherein the variant or mutant strains or bacterial cells comprise a disarmed pTiChry5 plasmid. The disarmed pTiChry5 plasmid may comprise a nucleic acid sequence at least 70% identical to the nucleic acid sequence of SEQ ID NO: 1, SEQ ID NO: 2, or SEQ ID NO: 3.

The present invention encompasses an *Agrobacterium* strain or cell of the invention which further comprises additional nucleic acid molecules, wherein the additional nucleic acid molecules may be a booster plasmid, a helper plasmid, a virulence-enhancing plasmid, and/or a binary vector. An *Agrobacterium* strain or cell of the invention may comprise at least one or more than one of the additional nucleic acid molecules described above.

In some embodiments, an *Agrobacterium* strain or cell of the invention may have at least one mutation on its bacterial chromosome. The mutation may be an insertion, deletion, or substitution. In some embodiments, an *Agrobacterium* strain or cell of the invention may harbor a significant (for example, greater than 1, 2, 3, 4, 5, 10, 15, 20, or 25 nucleotides in length) chromosomal insertion. The present invention embodies a variant or mutant of an *Agrobacterium* strain or cell of the invention which comprises an insertion within its chromosome, wherein the insertion comprises a gene which encodes for a protein capable of enhancing transformation efficacy of the *Agrobacterium* cell, transformation efficacy of a host cell such as a plant cell, or virulence of the *Agrobacterium* cell. A Chry5d1, Chry5d2, or Chry5d3 strain which comprises a chromosomal insertion is considered an obvious variant of these strains and is recognized as a strain of the invention.

The present invention encompasses methods for delivering DNA into a host cell. The host cell may be a eukaryotic cell. The host cell may further be a plant cell or a fungal cell. One method of the invention comprises (a) introducing a binary vector comprising a gene of interest into an *Agrobacterium* cell of the invention, to produce a recombinant *Agrobacterium* cell; and (b) contacting said recombinant *Agrobacterium* cell with the host cell under conditions that permit the *Agrobacterium* cell to transform the host cell.

The prevent invention also embodies a method for delivering recombinant protein into a host cell comprising the steps of: (a) introducing a recombinant protein expression cassette into an *Agrobacterium* cell of the invention to produce a recombinant *Agrobacterium* cell; and (b) contacting said recombinant *Agrobacterium* cell with the host cell under conditions that permit the *Agrobacterium* cell to deliver recombinant protein to the host cell. The host cell may be a eukaryotic cell. The host cell may further be a plant cell or a fungal cell.

The present invention also encompasses a method for producing a transgenic host cell comprising the steps of: (a) providing an *Agrobacterium* cell of the invention, further comprising a transgenic T-DNA region; and (b) contacting said recombinant *Agrobacterium* cell with a host cell, under conditions that permit the *Agrobacterium* cell to transform the host cell.

For the methods of the invention, the host cell may be a eukaryotic cell. The host cell may further be a plant cell or a fungal cell. The plant cell may be from a tissue selected from the group consisting of: embryogenic plant tissue, organogenic plant tissue, vegetative plant tissue, callus tissue, and reproductive tissue. The plant cell may be a cell from a plant part selected from the group consisting of: pollen; ovule; immature plant embryo; mature plant embryo; seed; seedling; root; cotyledon; stem; node; internode; bud; leaf; shoot apical meristem; floral meristem; flower buds; inflorescence; and cultured plant material. The plant cell may be a dicotyledonous, monocotyledonous, or gymnosperm cell. The plant cell may be a soybean cell or a maize cell.

In other embodiments, a method of the invention may encompass a T-DNA comprising one or more plant expressible gene(s) of interest and/or regulatory gene(s) of interest. In other embodiments, a method of the invention may encompass a T-DNA comprising a nucleic acid molecule encoding for at least one genome editing nuclease. Any genome editing nucleases known in the art may be used, including but not limited to Zinc-finger nucleases (ZFNs), transcription activator-like effector nucleases (TALEN s), and clustered regularly interspaced short palindromic repeat (CRISPR)/Cas-based RNA-guided DNA endonucleases, such as Cas9 or Cpf1.

In other embodiments of a method of the invention, the step of contacting the *Agrobacterium* cell with the plant cell may be accomplished by at least one method selected from the group consisting of: incubating the plant cell, plant tissue, or plant with *Agrobacterium*; co-cultivation of the at least one plant host cell and the *Agrobacterium*; floral dip method; vacuum infiltration method; cotyledonary-node method; and sonication-assisted *Agrobacterium*-mediated transformation. The step of contacting the *Agrobacterium* cell with the plant cell may also be accomplished by any combination of the methods listed above.

The present invention also encompasses a method of the invention described above, further comprising isolating or selecting for a host cell comprising the transgenic T-DNA. This is a transgenic host cell. The present invention also encompasses the transgenic cell produced by a method of the invention. The present invention also encompasses a transgenic plant produced by a method of the invention.

The present invention also embodies a nucleic acid molecule comprising a nucleic acid sequence at least 70% identical to SEQ ID NO: 1, SEQ ID NO: 2, or SEQ ID NO: 3. In another embodiment, the present invention includes a disarmed pTiChry5 plasmid comprising a sequence at least 70% identical to SEQ ID NO: 1, SEQ ID NO: 2, or SEQ ID NO: 3. All of these described nucleic acid molecules are not naturally occurring and are created by the hand of man, as described in Examples 2 and 3. The present invention also embodies a cell comprising these nucleic acid molecules. The cell may be a eukaryotic or prokaryotic cell. The cell may be an *Agrobacterium* cell.

In other embodiments, an *Agrobacterium* strain or cell of the invention, for example *A. tumefaciens* strains Chry5d1, Chry5d2, and Chry5d3, are capable of introducing genome editing nucleases into a plant cell, plant tissue, or plant. In such embodiments, transgenic T-DNA contains one or more nuclease-encoding genes. Expressed in the plant cell, plant tissue, or plant, the genome editing nucleases aid in the insertion of a gene of interest or regulatory gene of interest, replace a native gene with a gene of interest or regulatory gene of interest, or remove or modify a native gene or native regulatory gene. Preferably, the encoded nucleases are targeted to a specific position in the plant's genome. Introducing genome editing nucleases into a plant cell, plant tissue, or plant can provide for trait stacking, resulting in the physical linkage of certain traits to ensure co-segregation during breeding. In yet another preferred embodiment *A. tumefaciens* strains Chry5d1, Chry5d2, and Chry5d3 are further modified to increase transformation efficiency, such as by altering vir gene expression and/or induction thereof. This may be realized by the presence of mutant or chimeric virA or virG genes. Combinations with super-virulent plasmids are also possible, generating so-called super-virulent strains. Super-virulent strain variants may also be generated by employing pSBI super virulence plasmid derived vectors.

The present invention also embodies a method for modifying a target site in the genome of a cell, comprising using an *Agrobacterium* strain or cell of the invention to introduce into the cell: (a) a first nucleic acid comprising at least 16 contiguous nucleotides, wherein the at least 16 contiguous nucleotides have at least 80% identity with a target site in the genome of the cell, and further comprising a transgene; and (b) a second nucleic acid molecule comprising a nucleotide sequence encoding a nuclease for site-directed cleavage at a nuclease cleavage site in the genome of the cell adjacent to the nucleotide sequence in the genome of the cell that corresponds to the at least 16 contiguous nucleotides of (a), under conditions wherein expression of the second nucleic acid molecule can occur to produce the nuclease and the nuclease can cleave at the nuclease cleavage site in the genome of the cell and modify the target site in the genome of the cell.

Another embodiment of the present invention is a method of allelic replacement by targeted modification of a target genomic site in a cell, whereby the target genomic site comprises at least a fragment of a native gene, comprising using an *Agrobacterium* strain or cell of the invention to introduce into the cell: (a) a first nucleic acid molecule comprising a donor DNA molecule, which comprises at least 16 contiguous nucleotides at least 80% identical to a genomic nucleic acid sequence, and further comprises a modified nucleic acid molecule comprising a nucleic acid sequence modified from the native gene; and (b) a second nucleic acid molecule comprising a nucleotide sequence encoding a nuclease for site-directed cleavage at a nuclease cleavage site in the genome of the cell adjacent to the nucleotide sequence in the genome of the cell that corresponds to the at least 16 contiguous nucleotides of (a), under conditions wherein expression of the second nucleic acid molecule can occur to produce the nuclease and the nuclease can cleave the nucleotide sequence at the target genomic site, whereby the modified nucleic acid molecule is integrated at the target genomic site in the genome of the cell.

In further embodiments of the methods described above, the first and/or the second nucleic acid molecule may be transiently expressed in the cell. In other embodiments, the cell may be a plant cell. Another embodiment of the present invention is a method of producing a genome modified plant, plant part, or progeny thereof, said method comprising regenerating a plant from the plant cell produced by the methods described above. Another embodiment of the invention is a genome modified plant, plant part, or progeny thereof, produced by the methods described above.

In a particular embodiment, a kit comprises at least one aliquot or sample of an *Agrobacterium* strain of the invention, for example Chry5d1, Chry5d2, or Chry5d3. In another particular embodiment, the kit additionally comprises and at least one separate aliquot or sample comprising a binary plasmid, wherein the binary plasmid comprises a T-DNA region. In this embodiment, the T-DNA region of the binary plasmid preferably comprises right and left border sequences and minimal internal sequences. More preferably, the T-DNA region of the binary plasmid comprises no other T-DNA other than the right and left border sequences.

BRIEF DESCRIPTION OF THE DRAWINGS

FIG. 1 (FIG. 1) is a graphical illustration of the region of the pTiChry5 vector which comprises the TL-DNA and TR-DNA regions. Fg1 to Fg6 represent the DNA sequences that flank the TL-DNA and TR-DNA which were used to remove TL-DNA or TR-DNA via homologous recombination.

BRIEF DESCRIPTION OF THE SEQUENCES

SEQ ID NO: 1 is a nucleotide sequence of the engineered region of the pTiChry5 vector of *A. tumefaciens* Chry5d1. The TL-DNA and TR-DNA regions have been removed, as well as the ~18 kB of nucleotide sequence between the two.

SEQ ID NO: 2 is a nucleotide sequence of the engineered region of the pTiChry5 vector of *A. tumefaciens* Chry5d2. The TL-DNA and TR-DNA regions have been removed, however the ~18 kB of nucleotide sequence between the two is still present.

SEQ ID NO: 3 is a nucleotide sequence of the engineered region of the pTiChry5 vector of *A. tumefaciens* Chry5d3. The TL-DNA and TR-DNA regions have been removed, as well as the ~18 kB of nucleotide sequence between the two and additional sequence upstream of TL-DNA and downstream of TR-DNA SEQ ID NO: 4 to 36 are nucleotide sequences encoding primers and/or probes useful to the invention.

DETAILED DESCRIPTION OF THE INVENTION

The following is a detailed description of the invention provided to aid those skilled in the art in practicing the invention. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments of the invention will be apparent to those skilled in the art in light of the instant disclosure, which do not depart from the invention. Hence, the following descriptions are intended to illustrate some particular embodiments of the invention, and not to exhaustively specify all permutations, combinations and variations thereof. Those of ordinary skill in the art may make modifications and variations in the embodiments described herein without departing from the spirit or scope of the invention.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, and other references mentioned herein are incorporated by reference in their entirety.

For clarity, certain terms used in the specification are defined and presented as follows:

As used herein, "a." "an" or "the" can mean one or more than one. For example, a cell can mean a single cell or a multiplicity of cells.

As used herein, "and/or" refers to and encompasses any and all possible combinations of one or more of the associated listed items, as well as the lack of combinations when interpreted in the alternative (or).

Further, the term "about," as used herein when referring to a measurable value such as an amount of a compound or agent, dose, time, temperature, and the like, is meant to encompass variations of ±20%, ±10%, ±5%, ±1%, ±0.5%, or even ±0.1% of the specified amount.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

The term "*Agrobacterium*" as used herein refers to a soil-borne, Gram-negative, rod-shaped phytopathogenic bacterium. The cells are normally rod-shaped (0.6-1.0 µm by 1.5-3.0 µm), occur singly or in pairs, without endospore, and are motile by one to six peritrichous flagella. Considerable extracellular polysaccharide slime is usually produced during growth on carbohydrate-containing media.

The species of *Agrobacterium*, *A. tumefaciens* (syn. *A. radiobacter*), *A. rhizogenes*. *A. rubi* and *A. vitis*, together with *Allorhizobium undicola*, form a monophyletic group with all *Rhizobium* species, based on comparative 16S rDNA analyses. *Agrobacterium* is an artificial genus comprising plant-pathogenic species. The monophyletic nature of *Agrobacterium*, *Allorhizobium* and *Rhizobium* and their common phenotypic generic circumscription support their amalgamation into a single genus, *Rhizobium*. The classification and characterization of *Agrobacterium* strains including differentiation of *A. tumefaciens* and *A. rhizogenes* and their various opine-type classes is a practice well known in the art (see, for example, Laboratory guide for identification of plant pathogenic bacteria, 3rd edition. (2001) N. W. Schaad, J. B. Jones, and W. Chun (eds.) ISBN 0890542635; for example, the article of Moore et al. published therein).

Recent analyses demonstrate that classification by its plant-pathogenic properties is not justified. Accordingly more advanced methods based on genome analysis and comparison (such as 16S rRNA sequencing; RFLP, Rep-PCR, etc.) are employed to elucidate the relationship of the various strains. Agrobacteria can be differentiated into at least three biovars, corresponding to species divisions based on differential biochemical and physiological tests. Pathogenic strains of *Agrobacterium* share a common feature; they contain at least one large plasmid, the tumor- or root-inducing (Ti- and Ri-, respectively) plasmid. Virulence is determined by different regions of the plasmid including the transferred DNA (T-DNA) and the virulence (vir) genes. The virulence genes mediate transfer of T-DNA into infected plant cells, where it integrates into the plant DNA. According to the "traditional" classification, Agrobacteria include, but are not limited to, strains of *Agrobacterium tumefaciens*, (which by its natural, "armed" Ti-plasmid typically causes crown gall in infected plants). *Agrobacterium rhizogenes* (which by its natural, "armed" Ri-plasmid causes hairy root disease in infected host plants), *Agrobacterium rubi* (which in its natural, "armed" form causes cane gall on *Rubus*). *Agrobacterium vitis*, and *Agrobacterium radiobacter*. The *Agrobacterium tumefaciens* cells and strains of the present invention does not comprise a wild-type Ti plasmid and/or a wild-type Ri plasmid.

The subject of the invention comprises three novel fully disarmed *A. tumefaciens* cells or strains, namely Chry5d1, Chry5d2, and Chry5d3. Cultures of these microbes have been deposited with the American Type Culture Collection (ATCC). 10801 University Blvd., Manassas. Va. 20110-2209 USA. The deposit for Chry5d1 has been assigned accession number ATCC No. PTA-124251 by the repository and was deposited on Aug. 1, 2017. The deposit for Chry5d2 has been assigned accession number ATCC No. PTA-124004 by the repository and was deposited on Aug. 1, 2017. The deposit for Chry5d3 has been assigned accession number ATCC No. PTA-124005 by the repository and was deposited on Aug. 1, 2017. The subject cultures have been deposited under conditions that assure that, upon request, access to the cultures will be available during the pendency of this patent application to one determined by the Commissioner of Patents and Trademarks to be entitled thereto under 37 CFR 1.14 and 35 § U.S.C 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposit will be stored and made available to the public in accord with the provisions of the Budapest Treaty for the Deposit of Microorganisms. Upon granting of a patent on any claims in the application, the Applicants will make the deposits available to the public pursuant to 37 CFR § 1.808. Additionally, Applicants will meet the requirements of 37 CFR § 1.801-1.809, including providing an indication of the viability of the samples when the deposits are made. The ATCC deposits will be maintained in that depository, which is a public depository, for a period of 30 years, or 5 years after the last request, or for the enforceable life of the patent, whichever is longer, and will each be replaced if it becomes nonviable during that period.

Until the present application, there was neither a report of a fully disarmed Chry5 strain nor the documented use of such a strain in plant transformation. The fully disarmed Chry5 strains of the invention are advantageous for generating transgenic plants that satisfy global regulatory and commercial requirements. A fully disarmed Chry5 strain is non-tumorigenic to the host cell it infects. Additionally, the fully disarmed Chry5 strains of the invention retain the chromosomal background and components of the pTiChry5 vector which contribute to the supervirulence of the Chry5 strain.

The present invention provides compositions and methods for *Agrobacterium*-mediated transformation. The present invention provides an isolated *Agrobacterium* strain or cell comprising a disarmed pTiChry5 vector, wherein the disarmed pTiChry5 vector comprises a nucleic acid sequence at least 70% identical to SEQ ID NO: 1, SEQ ID NO: 2, or SEQ ID NO: 3. The invention further provides a bacterial cell of the *Agrobacterium* strain. The invention further provides an engineered *Agrobacterium tumefaciens* cell comprising the Chry5 strain chromosomal background and a fully disarmed pTiChry5 vector, wherein the disarmed pTiChry5 vector has both TL-DNA and TR-DNA regions removed. The invention further comprises an *A. tumefaciens* cell comprising a fully disarmed pTiChry5 vector, wherein the vector comprises a nucleic acid sequence at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 1, SEQ ID NO: 2, or SEQ ID NO: 3. The invention further provides *A. tumefaciens* strains Chry5d1, Chry5d2, and Chry5d3, wherein representative samples of each strain have been deposited as ATCC Accession Nos. PTA-124251, PTA-124004, and PTA-124005, respectively. Strains Chry5d1, Chry5d2, and Chry5d3 each comprise disarmed variants of the pTiChry5 vector. Strain Chry5d3 comprises a fully disarmed variant of the pTiChry5 vector. The invention also provides strain Chry5d2 which comprises a disarmed pTiChry5 vector, wherein the nucleic acid sequence of said vector is SEQ ID NO: 1. The invention also provides strain Chry5d3 which comprises a fully disarmed pTiChry5 vector, wherein the nucleic acid sequence of said vector is SEQ ID NO: 2. The invention also provides strain Chry5d1 which comprises a fully disarmed pTiChry5 vector, wherein the sequence of said vector is SEQ ID NO: 3. The invention further provides isolated strains and bacterial cells thereof.

The invention also provides variant or mutant strains or bacterial cells of Chry5d1, Chry5d2, or Chry5d3, wherein the variant or mutant strains or bacterial cells comprise a fully disarmed pTiChry5 plasmid. The fully disarmed pTiChry5 plasmid may comprise a nucleic acid sequence at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 1, SEQ ID NO: 2, or SEQ ID NO: 3.

As used herein, a bacterial strain such as an *Agrobacterium* strain is an isolate or group of isolates that can be distinguished from other isolates of the same genus and species by phenotypic characteristics, genotypic characteristics, or both (Tenover et al., 1995, J Clin Microbiol 33:2233-2239). As used herein, clones or bacterial clones, such as *Agrobacterium* clones, are isolates that are indistinguishable from each other by a variety of genetic tests, or that are so similar that they are presumed to be derived from a common parent (Tenover et al., 1995). Bacterial strains or clones may contain member bacterial cells which carry mutations such that they are not completely genetically identical.

As used herein, a variant of a strain is typically a genetically altered version derivative of the initial strain, such that it is closely related to the initial strain and has the majority of the same phenotypic and/or genotypic characteristics. For example, a recA– Chry5d2 strain is a variant of the Chry5d2 strain, in which the recA gene has been disabled. A second example of a Chry5d2 variant is a Chry5d2 strain which comprises an introduced additional copy of a vir gene within its chromosomal genome.

As used herein, reference to "isolated" means that the strain is removed from the environment in which it exists in nature. Thus, the isolated strain may exist as, for example, a biologically pure culture or colony, or in association with an agricultural carrier. An isolated bacterial strain, such as an isolated *Agrobacterium* strain, is made up of the descendants of a single isolation in pure culture and usually is made up of a succession of cultures ultimately derived from an initial single colony (as described in Bergey's Manual of Systematic Bacteriology). As used herein, a strain is not a natural concept nor does it occur in nature, as the selection of the 'initial single colony' is made by the hand of man and its descendants are kept in artificial culture.

As used herein the term "substantially biologically pure" means that a culture fluid, culture plate, or other collection of materials (e.g., bacteria, DNA, RNA, plasmid) is homogenous or uniformly of a single form of the material (e.g., single strain of bacteria, DNA, RNA, or plasmid), with greater that 90% purity, preferably at least 95% pure, and more preferably at least 98%.

As used herein, the term "comprising" further contemplates scenarios in which the composition and/or method "consists of" or "consists essentially of" the recited components and/or steps. As used herein, reference to "consists essentially of" refers to the situation where additional components and/or steps are only those that do not affect the transformation efficiency of the composition and/or method.

In specific embodiments, the subject invention provides bacterial strains, examples of which are deposited at the ATCC with accession numbers PTA-124251, PTA-124004, and PTA-124005, and mutants thereof. Procedures for making mutants are well known in the microbiological art. For example, ultraviolet light and nitrosoguanidine are used extensively toward this end.

*Agrobacterium* is well-known as an agent of horizontal gene transfer that plays an essential role in basic scientific research and in agricultural biotechnology. In the 1980s, scientists learned to disarm (by deleting the oncogenes and, usually, the opine synthase genes) virulent *Agrobacterium* strains such that tissues transformed by the bacteria could regenerate into normal plants, free of the oncogenes that caused either gall growth or hairy root formation. Inserting genes of interest (transgenes) in the place of oncogenes and opine synthase genes resulted in plants expressing these genes of interest and, thus, novel phenotypes. Although initially conducted in cis (i.e. transgenes were placed within T-DNA of native Ti-plasmids), the development of binary systems, in which T-DNA and virulence helper plasmids were separated into two different vectors, greatly increased the utility of *Agrobacterium* as a vehicle for gene transfer.

The binary vector systems offer a great degree of flexibility, since they do not require a specifically engineered Ti plasmid with a homologous recombination site. A disarmed *Agrobacterium* strain, wherein the T-DNA region is modified or removed completely, can be used to transfer genes for any binary vector. Due to their versatility, binary vectors are the preferred intermediate vectors for cloning genes destined for *Agrobacterium*-mediated transformation in plants. However, it is preferable that strains of *Agrobacterium* to be used with binary vectors have its own disarmed Ti plasmid, especially if the target plant species in inefficiently transformed by *Agrobacterium*. Otherwise, the gene(s) of interest from the binary vector may be co-transformed along with the tumor-inducing genes from the native T-DNA of the bacteria, possibly reducing transformation efficiency of the target gene(s) and also producing tumorigenic disease symptoms in many of the target host cells, thereby preventing differentiation of these cells into normal plants.

A "fully disarmed Ti plasmid" or "fully disarmed Ti vector" is a plasmid produced by removing the T-DNA region(s) from a wild-type Ti plasmid. *Agrobacterium* strains harboring a disarmed Ti plasmid (and no other wild-type Ti plasmid) are referred to as disarmed *Agrobacterium* strains. Such strains are non-oncogenic, and can be used for transformation of plants.

In some embodiments, the *A. tumefaciens* strains of the invention comprises a binary vector. A binary vector is a plasmid comprising a T-DNA which comprises a nucleic acid molecule, for example DNA that is desirable to be introduced into the genome of a host cell. This vector can be replicated in both *Agrobacterium* strains and *Escherichia. coli*. Specific examples of binary vectors include pBIN19, pBI121, pK3T21, pIG121Hm, pLC41, vectors of pGreen series, vectors of pCLEAN-G series, vectors of pPZP series, vectors of pCAMBIA series, pOREOII, pGWB or the like. The DNA to be inserted into the T-DNA region of the binary vector, also referred to as the transgene, is not particularly limited. For example, it is possible to use any DNA, such as a genome DNA fragment, or a cDNA fragment. A non-limiting size of the DNA is 0.1 kb-100 kb, and more preferably 1 kb-40 kb. The transgene may comprise the nucleic acid coding sequence of a gene of interest, a regulatory gene, a marker gene, a reporter gene, or combinations thereof.

In some embodiments, a Chry5 strain or cell of the invention also comprises a booster vector. A booster vector (U.S. Patent Publication 2016/0083737, herein incorporated by reference) may improve the gene introduction efficiency and/or the transformation efficiency when introduced into an *Agrobacterium* cell. The booster vector may comprise a virB gene (Ward et al., 1988, J Biol Chem 263: 5804-5814), a virC gene (Close et al., 1987, J Bacteriol 169: 2336-2344), a virD1 gene, a virD2 gene, a virD3 gene (virD genes are described in, for example. Ream. (2008. Production of a mobile T-DNA by *Agrobacterium tumefaciens*. In *Agrobacterium*. T. Tzfira and V. Citovsky. eds (New York: Springer Science+Business Media, LLC). pp. 280-313), a virG gene (Winans et al., 1986, PNAS 83: 8278-8282) and/or the virJ gene (Pantoja et al., 2002, Mol Microbiol 45: 1325-1335). The booster vector may further comprise a virE gene (Citovsky et al., 1988. Science 240: 501-504), a virD4 gene (Christie et al., 2004. Biochim Biopys Acta 1694: 219-234), and/or a virD5 gene (Vergunst et al., 2005, PNAS, 102: 832-837). It is well-known in the art that many of the vir genes are operons: therefore, for example, reference to "a virB gene" refers to at least one coding sequence or to all coding sequences of the virB gene operon. The booster vector also comprises an origin of replication such that the replication mechanism allows for mutual co-existence of the booster vector and the Ti plasmid. The booster vector may also comprise a selectable marker, for example a drug selectable marker gene such as a kanamycin resistance gene, an ampicillin resistance gene, a spectinomycin resistance gene, a tetracycline resistance gene, a hygromycin resistance gene, or various other drug selectable marker genes.

In some embodiments, the *A. tumefaciens* strains of the invention comprise a BIBAC (binary bacterial artificial chromosome) vector. BIBAC vectors were designed to enable efficient transformation of large DNA fragments into plant and non-plant host cells (reviewed in Shibata and Liu, 2000, Trends in Plant Science 5: 354-357).

The present invention encompasses an *Agrobacterium* strain or cell of the invention which further comprises additional nucleic acid molecules, wherein the additional nucleic acid molecules may be a booster plasmid, a helper plasmid, a virulence-enhancing plasmid, and/or a binary vector. An *Agrobacterium* strain or cell of the invention may comprise at least one or more than one of the additional nucleic acid molecules described above.

In some embodiments, an *Agrobacterium* strain or cell of the invention may have at least one mutation on its bacterial chromosome. The mutation may be an insertion, deletion, or substitution. In some embodiments, an *Agrobacterium* strain or cell of the invention may harbor a significant (for example, greater than 1, 2, 3, 4, 5, 10, 15, 20, or 25 nucleotides in length) chromosomal insertion. For example, it is known that the picA chromosomal locus of *Agrobacterium* strains EHA101 and GV3101 can be used as an integration site for gene of interest (Lee et al., 2001. Mol Plant Microbe Interact 14: 577-579). This locus can be used for insertion of gene(s) which can improve transformation efficiency of host cells, such as for example, additional copies of vir genes, such as virG or virD2, or to introduce antibiotic resistance genes. This locus can also be used for a launching site for T-DNA (Oltmanns et al., 2010, Plant Physiol 152: 1158-1166). Similarly, other chromosomal sites which can be used for integration sites are described in U.S. Pat. Nos. 6,323,396 and 9,617,551. The present invention embodies a variant or mutant of an *Agrobacterium* strain or cell of the invention which comprises an insertion within its chromosome, wherein the insertion comprises a gene which encodes for a protein capable of enhancing transformation efficacy of the *Agrobacterium* cell, transformation efficacy of a host cell such as a plant cell, or virulence of the *Agrobacterium* cell. A Chry5d1, Chry5d2, or Chry5d3 strain which comprises a chromosomal insertion is considered an obvious variant of these strains and is recognized as a strain of the invention.

In some embodiments, an *Agrobacterium* strain or cell of the invention may harbor a mutation to a chromosomal gene. For example, it is generally known in the art that *Agrobacterium* strains which are deficient in DNA recombination, which may otherwise result in instability or rearrangement of plant transformation binary vectors, are desirable. One example is a recA– *Agrobacterium* strain, such as for example Farrand et al. (1989. J Bacteriol 171: 5314-5321). *Agrobacterium* cells that are deficient in recA function are more prone to tolerate homologous DNA sequences without rearrangement or deletion. The present invention embodies variants or mutants of an *Agrobacterium* strain of the invention which harbor mutations to the recA gene. The present invention further embodies variants or mutants of an *Agrobacterium* strain of the invention wherein the recA gene has been inactivated. The present specification further describes recA-Chry5d2 and recA-Chry5d3 in the Examples section. Other chromosomal mutations may be made to improve the transformation efficiency, either of the *Agrobacterium* strain to be transformed with a vector (bacterial transformation efficiency), or of the ability of the *Agrobacterium* to transform a host cell. Such chromosomal genes may, for example, play a role in the expression of vir genes, be involved in membrane structure, or be involved in plant response.

Such chromosomal genes include ChvE, ChvG/I, ChrH, ChvD, citrate synthase, phosphoenolpyruvate carboxykinase (PckA). *Agrobacterium* outer membrane protein (AopB), Catalase (KatA), or the tRNA gene miaA (see Nester et al., 2015, Frontiers in Plant Science 5: Article 730). Additionally, mutations may be made to other *Agrobacterium* genes that have a role in DNA repair and/or in homologous recombination of DNA strands. Mutations to chromosomal genes of Chry5d, Chry5d2, and Chry5d3 are considered obvious variants of these stains and are further considered strains of the invention.

The term "plant" as used herein refers to a plurality of plant cells, which are largely differentiated into a structure that is present at any stage of a plant's development. Such structures include one or more plant organs including, but are not limited to, fruit, shoot, stem, leaf, flower petal, etc. Preferably, the term "plant" includes whole plants, shoot vegetative organs/structures (e.g. leaves, stems and tubers), roots, flowers and floral organs/structures (e.g. bracts, sepals, petals, stamens, carpels, anthers, and ovules), seeds (including embryo, endosperm, and seed coat), fruits (the mature ovary), plant tissues (e.g. vascular tissue, ground tissue, and the like), cells (e.g. guard cells, egg cells, trichomes and the like), and progeny of same. The class of plants that can be used in the methods of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous. Included within the scope of the invention are all genera and species of higher and lower plants of the plant kingdom. Included are furthermore the mature plants, seed, shoots and seedlings, and parts, propagation material (for example seeds and fruit), and cultures (e.g., cell cultures) derived therefrom.

Annual, perennial, gymnosperms, monocotyledonous and dicotyledonous plants are preferred host organisms for the generation of transgenic plants. The use of *Agrobacterium* strains and methods according to the invention is furthermore advantageous in crop plants, ornamental plants, forestry, fruit, ornamental trees, flowers, cut flowers, shrubs, and turf.

Plants useful for the purposes of the present disclosure may comprise for example, the Fabaceae family, such as pea, alfalfa and soybean; the Umbelliferae family, particularly the genus *Daucus* (very particularly the species *carota* (carrot)) and *Apium* (very particularly the species *graveolens* var. *dulce* (celery)); the Solanaceae family, particularly the genus *Lycopersicon*, very particularly the species *esculentum* (tomato) and the genus *Solanum*, very particularly the species *tuberosum* (potato) and *melongena* (aubergine, or eggplant); the Cruciferae family, particularly the genus *Brassica*, very particularly the species *napus* (oilseed rape), *campestris* (beet), *oleracea* cv Tastie (cabbage), *oleracea* cv Snowball Y (cauliflower) and *oleracea* cv Emperor (broccoli); and the Compositae family, particularly the genus *Lactuca*, very particularly the species *sativa* (lettuce). Plants useful for the purposes of the present disclosure may comprise for example, plants of the genera *Glycine; Medicago; Pisum; Beta, Helianthus; Arabidopsis; Dioscorea; Ipomea; Manihot; Plantago; Zea; Oryza; Sorghum; Triticum; Hordeum; Saccharum; Brassica; Solanum; Nicotiana; Gossypium; Vitis; Populus; Picea*; and *Pinus*.

The transgenic plants according to the invention are selected in particular among monocotyledonous crop plants, such as, for example, cereals such as wheat, barley, sorghum, millet, rye, triticale, maize, rice or oats, and sugarcane. A transgenic plant according to the invention may also be a monocotyledonous plant of a genus selected from the group consisting of: *Zea, Oryza, Sorghum, Triticum, Hordeum, Saccharum, Pennisetum, Avena, Brachypodium, Panicum, Agrostis, Festuca*, and *Dactylis*. Further preferred are trees such as apple, pear, quince, plum, cherry, peach, nectarine, apricot, *papaya*, mango, and other woody species including coniferous and deciduous trees such as poplar, pine, *sequoia*, cedar, oak, etc. Also preferred are *Arabidopsis thaliana, Nicotiana tabacum*, oilseed rape, soybean, corn (maize), wheat, linseed, potato and *Tagetes*.

A "plant cell" is a structural and physiological unit of a plant, comprising a protoplast and a cell wall. The plant cell may be in form of an isolated single cell or a cultured cell, or as a part of higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

"Plant material" refers to leaves, stems, roots, flowers or flower parts, fruits, pollen, egg cells, zygotes, seeds, cuttings, cell or tissue cultures, or any other part or product of a plant.

A "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any group of plant cells organized into structural and/or functional units. The use of this term in conjunction with, or in the absence of, any specific type of plant tissue as listed above or otherwise embraced by this definition is not intended to be exclusive of any other type of plant tissue.

The term "plant part" indicates a part of a plant, including single cells and cell tissues such as plant cells that are intact in plants, cell clumps and tissue cultures from which plants can be regenerated. Examples of plant parts include, but are not limited to, single cells and tissues from pollen, ovules, leaves, embryos, roots, root tips, anthers, flowers, fruits, stems, shoots, and seeds; as well as pollen, ovules, leaves, embryos, roots, root tips, anthers, flowers, fruits, stems, shoots, scions, rootstocks, seeds, protoplasts, calli, and the like.

Plant Transformation

The term "transformation" as used herein refers to the transfer of a nucleic acid fragment into the genome of a host cell, resulting in genetically stable inheritance. In some particular embodiments, the introduction into a plant, plant part and/or plant cell is via bacterial-mediated transformation, particle bombardment transformation, calcium-phosphate-mediated transformation, cyclodextrin-mediated transformation, electroporation, liposome-mediated transformation, nanoparticle-mediated transformation, polymermediated transformation, virus-mediated nucleic acid delivery, whisker-mediated nucleic acid delivery, microinjection, sonication, infiltration, polyethylene glycol-mediated transformation, protoplast transformation, or any other electrical, chemical, physical and/or biological mechanism that results in the introduction of nucleic acid into the plant, plant part and/or cell thereof, or a combination thereof.

Agrobacterium-mediated transformation is a commonly used method for transforming plants because of its high efficiency of transformation and because of its broad utility with many different species. Agrobacterium-mediated transformation typically involves transfer of the binary vector carrying the foreign DNA of interest to an appropriate Agrobacterium strain that may depend on the complement of vir genes carried by the host Agrobacterium strain either on a co-resident Ti plasmid or chromosomally (Uknes et al 1993, Plant Cell 5:159-169). The transfer of the recombinant binary vector to Agrobacterium can be accomplished by a tri-parental mating procedure using Escherichia coli carrying the recombinant binary vector and a helper E. coli strain that carries a plasmid that is able to mobilize the recombinant binary vector to the target Agrobacterium strain. Alternatively, the recombinant binary vector can be transferred to Agrobacterium by nucleic acid transformation (Hofgen and Willmitzer 1988, Nucleic Acids Res 16:9877).

Transformation of a plant by recombinant Agrobacterium usually involves co-cultivation of the Agrobacterium with explants from the plant and follows methods well known in the art. Efficiency of transformation with Agrobacterium can be enhanced by numerous methods known in the art, for example, wounding, vacuum infiltration, heat shock and/or centrifugation, addition of silver nitrate, sonication etc. In a preferred embodiment, the explant material is wounded prior to inoculation (co-cultivation) with Agrobacterium. Many methods of wounding can be used, including, for example, cutting, abrading, piercing, poking, penetration with fine particles or pressurized fluids, plasma wounding, application of hyperbaric pressure, or sonication. Wounding can be performed using objects such as, but not limited to, scalpels, scissors, needles, abrasive objects, airbrush, particles, electric gene guns, or sound waves. Another alternative is vacuum infiltration. Other methods to increase Agrobacterium transformation efficiency known in the art can be combined, including but not limited to sonication of the target tissue.

The Agrobacterium strains described herein are grown and used in a manner as known in the art. For example, an Agrobacterium strain of the invention further comprising a binary vector may be grown for 3 days in YEP medium supplemented with the appropriate antibiotic (e.g., 50 mg/L kanamycin). Bacteria may be collected by centrifugation and resuspended. In a particular embodiment, Agrobacterium cultures are started by use of aliquots frozen at −80° C. Agrobacterium may be resuspended in the medium used for culture of plant tissues.

The concentration of Agrobacterium used for infection and co-cultivation may need to be varied. Thus, a range of Agrobacterium concentrations from 102 to 1010 cfu/mL and a range of co-cultivation periods from a few hours to 14 days can be used. Plant material may be inoculated with the Agrobacterium culture for a few minutes to a few hours, typically about 10 minutes to 3 hours. The excess media is then drained and the Agrobacterium are permitted to co-cultivate with the target host tissue for several days, generally carried out for 1 to 14, preferably 2 to 4 days. During this step, the Agrobacterium contacts a host cell, for example a plant cell, and transfers the genes within the T-DNA into the target host cell. Normally no selection agent presents during this step.

It is possible, although not necessary, to employ one or more phenolic compounds in the medium prior to or during the Agrobacterium co-cultivation. "Plant phenolic compounds" or "plant phenolics" suitable within the scope of the invention are those isolated substituted phenolic molecules which are capable to induce a positive chemotactic response, particularly those who are capable to induce increased vir gene expression in a Ti plasmid-containing strain of Agrobacterium. Preferred is acetosyringone. Moreover, certain compounds, such as osmoprotectants (e.g. L-proline preferably at a concentration of about 700 mg/L or betaine), phytohormones (inter alia NAA), opines, or sugars, are expected to act synergistically when added in combination with plant phenolic compounds. The plant phenolic compound, particularly acetosyringone, can be added to the medium prior to contacting the starting material with Agrobacterium (for e.g., several hours to one day). Possible concentrations of plant phenolic compounds in the medium range from about 25 µM to 700 µM, preferably 100-200 µM.

Supplementation of the co-cultivation medium with antioxidants (e.g., dithiothreitol, L-cysteine) which can decrease tissue necrosis due to plant defense responses (like phenolic oxidation) may further improve the efficiency of Agrobacterium-mediated transformation.

After co-cultivation, steps can be included to remove, suppress growth, or kill the Agrobacterium. These steps may include one or more washing steps. The medium employed after the co-cultivation step preferably contains an antibiotic. This step is intended to kill the remaining Agrobacterium cells. Preferred antibiotics to be employed are, for example, carbenicillin (500 mg/L) or Timentin™ (GlaxoSmithKline; a mixture of ticarcillin disodium and clavulanate potassium; 0.8 g Timentin™ contains 50 mg clavulanic acid with 750 mg ticarcillin).

After the co-cultivation step, the co-cultivated starting material is preferably incubated on a regeneration medium comprising at least one plant growth factor. The employed media may further contain at least one compound, which in combination with the selectable marker gene allows for identification and/or selection of plant cells (e.g., a selective agent) may be applied. Starting material may be incubated for a certain time (e.g., 5 to 14 days) after the cocultivation step on a medium lacking a selection compound. Establishment of a reliable resistance level against the selection compound may need some time to prevent unintended damage by the selection compound.

Transformed tissue is typically regenerated on selection medium carrying an antibiotic or herbicide resistance marker between the binary plasmid T-DNA borders. Plant regeneration from plant cells, plant tissue culture and/or cultured protoplasts is described, for example, in Evans et al. (*Handbook of Plant Cell Cultures*, Vol. 1, MacMilan Publishing Co. New York (1983)); and Vasil I. R. (ed.) (*Cell Culture and Somatic Cell Genetics of Plants*, Acad. Press, Orlando, Vol. I (1984), and Vol. II (1986)). Methods of selecting for transformed transgenic plants, plant cells and/or plant tissue culture are routine in the art and can be employed in the methods of the invention provided herein.

By "stably introducing" or "stably introduced" in the context of a polynucleotide introduced into a cell is intended the introduced polynucleotide is stably incorporated into the genome of the cell, and thus the cell is stably transformed with the polynucleotide.

"Stable transformation" or "stably transformed" as used herein means that a nucleic acid is introduced into a cell and integrates into the genome of the cell. As such, the integrated nucleic acid is capable of being inherited by the progeny thereof, more particularly, by the progeny of multiple successive generations. "Genome" as used herein also includes the nuclear and the plastid genome, and therefore includes integration of the nucleic acid into, for example, the chloroplast genome. Stable transformation as used herein can also refer to a transgene that is maintained extrachromosomally, for example, as a minichromosome.

Stable transformation of a cell can be detected by, for example, a Southern blot hybridization assay of genomic DNA of the cell with nucleic acid sequences which specifically hybridize with a nucleotide sequence of a transgene introduced into an organism (e.g., a plant). Stable transformation of a cell can be detected by, for example, a Northern blot hybridization assay of RNA of the cell with nucleic acid sequences which specifically hybridize with a nucleotide sequence of a transgene introduced into a plant or other organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods Transformation can also be detected by direct sequencing and/or hybridization protocols well known in the art.

The "transformation and regeneration process" refers to the process of stably introducing a transgene into a plant cell and regenerating a plant from the transgenic plant cell. As used herein, transformation and regeneration includes the selection process, whereby a transgene comprises a selectable marker and the transformed cell has incorporated and expressed the transgene, such that the transformed cell will survive and developmentally flourish in the presence of the selection agent. "Regeneration" refers to growing a whole plant from a plant cell, a group of plant cells, or a plant piece such as from a protoplast, callus, or tissue part.

A "selectable marker" or "selectable marker gene" refers to a gene whose expression in a plant cell gives the cell a selective advantage. "Positive selection" refers to a transformed cell acquiring the ability to metabolize a substrate that it previously could not use or could not use efficiently, typically by being transformed with and expressing a positive selectable marker gene. This transformed cell thereby grows out of the mass of nontransformed tissue. Positive selection can be of many types from inactive forms of plant growth regulators that are then converted to active forms by the transferred enzyme to alternative carbohydrate sources that are not utilized efficiently by the nontransformed cells, for example mannose, which then become available upon transformation with an enzyme, for example phosphomannose isomerase, that allows them to be metabolized. Non-transformed cells either grow slowly in comparison to transformed cells or not at all. Other types of selection may be due to the cells transformed with the selectable marker gene gaining the ability to grow in presence of a negative selection agent, such as an antibiotic or an herbicide, compared to the ability to grow of non-transformed cells. A selective advantage possessed by a transformed cell may also be due to the loss of a previously possessed gene in what is called "negative selection". In this, a compound is added that is toxic only to cells that did not lose a specific gene (a negative selectable marker gene) present in the parent cell (typically a transgene).

Examples of selectable markers include, but are not limited to, genes that provide resistance or tolerance to antibiotics such as kanamycin (Dekeyser et al. 1989, Plant Phys 90: 217-23), spectinomycin (Svab and Maliga 1993, Plant Mol Biol 14: 197-205), streptomycin (Maliga et al. 1988, Mol Gen Genet 214: 456-459), hygromycin B (Waldron et al. 1985, Plant Mol Biol 5: 103-108), bleomycin (Hille et al. 1986, Plant Mol Biol 7: 171-176), sulphonamides (Guerineau et al. 1990, Plant Mol Biol 15: 127-136), streptothricin (Jelenska et al. 2000, Plant Cell Rep 19: 298-303), or chloramphenicol (De Block et al. 1984, EMBO J 3: 1681-1689). Other selectable markers include genes that provide resistance or tolerance to herbicides, such as the S4 and/or Hra mutations of acetolactate synthase (ALS) that confer resistance to herbicides including sulfonylureas, imidazolinones, triazolopyrimidines, and pyrimidinyl thiobenzoates; 5-enol-pyrovyl-shikimate-3-phosphate-synthase (EPSPS) genes, including but not limited to those described in U.S. Pat. Nos. 4,940,935, 5,188,642, 5,633,435, 6,566,587, 7,674,598 (as well as all related applications) and the glyphosate N-acetyltransferase (GAT) which confers resistance to glyphosate (Castle et al. 2004, Science 304:1151-1154, and U.S. Patent Application Publication Nos. 20070004912, 20050246798, and 20050060767); BAR which confers resistance to glufosinate (see e.g., U.S. Pat. No. 5,561,236); aryloxy alkanoate dioxygenase or AAD-1, AAD-12, or AAD-13 which confer resistance to 2,4-D; genes such as *Pseudomonas* HPPD which confer HPPD resistance; Sprotophorphyrinogen oxidase (PPO) mutants and variants, which confer resistance to peroxidizing herbicides including fomesafen, acifluorfen-sodium, oxyfluorfen, lactofen, fluthiacet-methyl, saflufenacil, flumioxazin, flumiclorac-pentyl, carfentrazone-ethyl, sulfentrazone); and genes conferring resistance to dicamba, such as dicamba monoxygenase (Herman et al. 2005, J Biol Chem 280: 24759-24767 and U.S. Pat. No. 7,812,224 and related applications and patents). Other examples of selectable markers can be found in Sundar and Sakthivel (2008, J Plant Physiology 165: 1698-1716), herein incorporated by reference.

Other selection systems include using drugs, metabolite analogs, metabolic intermediates, and enzymes for positive selection or conditional positive selection of transgenic plants. Examples include, but are not limited to, a gene encoding phosphomannose isomerase (PMI) where mannose is the selection agent, or a gene encoding xylose isomerase where D-xylose is the selection agent (Haldrup et al. 1998, Plant Mol Biol 37: 287-96). Finally, other selection systems may use hormone-free medium as the selection agent. One non-limiting example the maize homeobox gene kn1, whose ectopic expression results in a 3-fold increase in transformation efficiency (Luo et al. 2006, Plant Cell Rep 25: 403-409). Examples of various selectable markers and genes encoding them are disclosed in Miki and McHugh (J Biotechnol, 2004, 107: 193-232; incorporated by reference).

In some embodiments of the invention, the selectable marker may be plant derived. An example of a selectable marker which can be plant derived includes, but is not limited to, 5-enolpyruvylshikimate-3-phosphate synthase (EPSPS). The enzyme 5-enolpyruvylshikimate-3-phosphate synthase (EPSPS) catalyzes an essential step in the shikimate pathway common to aromatic amino acid biosynthesis in plants. The herbicide glyphosate inhibits EPSPS, thereby killing the plant. Transgenic glyphosate-tolerant plants can be created by the introduction of a modified EPSPS transgene which is not affected by glyphosate (for example, U.S. Pat. No. 6,040,497; incorporated by reference). Other examples of a modified plant EPSPS which can be used as a selectable marker in the presence of glyphosate includes a P106L mutant of rice EPSPS (Zhou et al 2006, Plant Physiol 140: 184-195) and a P106S mutation in goosegrass EPSPS (Baerson et al 2002, Plant Physiol 129: 1265-1275). Other sources of EPSPS which are not plant derived and can be used to confer glyphosate tolerance include but are not limited to an EPSPS P101S mutant from *Salmonella typhimurium* (Comai et al 1985, Nature 317: 741-744) and a mutated version of CP4 EPSPS from *Agrobacterium* sp. Strain CP4 (Funke et al 2006, PNAS 103: 13010-13015). Although the plant EPSPS gene is nuclear, the mature enzyme is localized in the chloroplast (Mousdale and Coggins 1985, Planta 163:241-249). EPSPS is synthesized as a preprotein containing a transit peptide, and the precursor is then transported into the chloroplast stroma and proteolytically processed to yield the mature enzyme (della-Cioppa et al. 1986, PNAS 83: 6873-6877). Therefore, to create a transgenic plant which has tolerance to glyphosate, a suitably mutated version of EPSPS which correctly translocates to the chloroplast could be introduced. Such a transgenic plant then has a native, genomic EPSPS gene as well as the mutated EPSPS transgene. Glyphosate could then be used as a selection agent during the transformation and regeneration process, whereby only those plants or plant tissue that are successfully transformed with the mutated EPSPS transgene survive.

Soybean plant material can be suitably transformed and fertile plants regenerated by many methods which are well known to one of skill in the art. For example, fertile morphologically normal transgenic soybean plants may be obtained by: 1) production of somatic embryogenic tissue from, e.g., immature cotyledon, hypocotyl or other suitable tissue; 2) transformation by particle bombardment or infection with *Agrobacterium*; and 3) regeneration of plants. In one example, as described in U.S. Pat. No. 5,024,944, cotyledon tissue is excised from immature embryos of soybean, optionally with the embryonic axis removed, and cultured on hormone-containing medium so as to form somatic embryogenic plant material. This material is transformed using, for example, direct DNA methods, DNA coated microprojectile bombardment or infection with *Agrobacterium*, cultured on a suitable selection medium and regenerated, optionally also in the continued presence of selecting agent, into fertile transgenic soybean plants. Selection agents may be antibiotics such as kanamycin, hygromycin, or herbicides such as an HPPD inhibitor, phosphinothricin, or glyphosate or, alternatively, selection may be based upon expression of a visualiable marker gene such as GUS. Target host tissues for transformation include meristematic tissue, somaclonal embryogenic tissue, and flower or flower-forming tissue. Other examples of soybean transformation include physical DNA delivery methods, such as particle bombardment (see e.g., Finer & McMullen, In Vitro Cell Dev. Biol., 1991, 27P:175-182; McCabe et al., Bio/technology, 1998, 6:923-926), whisker (Khalafalla et al., African J. of Biotechnology, 2006, 5:1594-1599), aerosol bean injection (U.S. Pat. No. 7,001,754), or by *Agrobacterium*-mediated delivery methods (Hinchee et al., Bio/Technology, 1988, 6:915-922; U.S. Pat. No. 7,002,058; U.S. Patent Application Publication Nos. 20040034889 and 20080229447; Paz et al., Plant Cell Report, 2006, 25:206-213).

Soybean (*Glycine max* L Merr.) has proven to be very difficult to transform with *A. tumefaciens*, at least in part because it is refractory to infection by wild-type *A. tumefaciens*. Comparative studies with a number of soybean cultivars and *A. tumefaciens* strains suggest that soybean susceptibility to *A. tumefaciens* is limited, and is both cultivar- and bacterial strain dependent (Bush 1991; Byrne 1987; Hood 1987). The problems with soybean recalcitrance to *A. tumefaciens* are further complicated by the difficulty of working with soybean in tissue culture. Despite some advances to date, however, *Agrobacterium*-mediated transformation in soybean remains inefficient and labor-intensive, and methods for improving that efficiency are continually being sought. The *Agrobacterium* strains and cell of the present invention and methods of using these in plant transformation address this problem, amongst others.

Thus, in another embodiment of the invention. *Agrobacterium* strains or cells of the invention, for example *A. tumefaciens* strains Chry5d1, Chry5d2, and Chry5d3, are capable of transforming plant cells, plant tissues, and plants, by mediating T-DNA transfer into the plant genome. In especially preferred embodiments, the *Agrobacterium* strain or cell of the invention lacks tumor inducing properties. The *A. tumefaciens* strains of the invention provide all functions required for plant cell infection and transformation but lack tumor inducing DNA sequences.

The present invention encompasses methods for delivering DNA into a host cell. The host cell may be a eukaryotic cell. The host cell may further be a plant cell or a fungal cell. One method of the invention comprises (a) introducing a binary vector comprising a gene of interest into an *Agrobacterium* cell of the invention, to produce a recombinant *Agrobacterium* cell; and (b) contacting said recombinant *Agrobacterium* cell with the host cell under conditions that permit the *Agrobacterium* cell to transform the host cell. As described above, co-cultivation allows for the *Agrobacterium* cell of the invention to contact a host cell and subsequently transfer the genes within the T-DNA of the binary vector into a host cell. In some embodiments, the binary vector comprises a plant expression cassette encoding for an enzyme capable of site-directed nucleic acid modification of a targeted site in the genome of the host cell. The expression cassette encoding for this enzyme may be introduced, or transformed, into the host cell. In further embodiments, expression of the site-directed nucleic acid modification enzyme can occur in the transformed host cell to produce a nucleic acid modification at the targeted site in the genome of the host cell. The host cell may be a eukaryotic cell. The host cell may further be a plant cell, fungal cell, or animal cell.

The prevent invention also embodies a method for delivering recombinant protein into a host cell comprising the steps of: (a) introducing a recombinant protein expression cassette into an *Agrobacterium* cell of the invention to produce a recombinant *Agrobacterium* cell; and (b) contacting said recombinant *Agrobacterium* cell with the host cell under conditions that permit the *Agrobacterium* cell to deliver recombinant protein to the host cell. The host cell may be a eukaryotic cell. The host cell may further be a plant cell, fungal cell, or animal cell. In some embodiments, the recombinant protein expression cassette comprises a nucleic acid sequence encoding for a chimeric site-directed DNA modification enzyme comprising a type 3 secretion signal (T3SS) or type 4 secretion signal (T4SS) for translocating into plant, fungal or animal host cell. The chimeric site-directed DNA modification enzyme is capable of producing a nucleic acid modifications of a targeted site in the genome of the host cell. The chimeric site-directed DNA modification enzyme may then be expressed in the *Agrobacterium* cell. The *Agrobacterium* cell may then be contacted with a plant, fungal, or animal host cell, such that the chimeric enzyme is delivered into the host cell and produces DNA modifications at targeted genomic sites in the genome of the host cell.

The present invention also encompasses a method for producing a transgenic host cell comprising the steps of: (a) providing an *Agrobacterium* cell of the invention, further comprising a transgenic T-DNA region; and (b) contacting said recombinant *Agrobacterium* cell with a host cell, under conditions that permit the *Agrobacterium* cell to transform the host cell.

For the methods of the invention, the host cell may be a eukaryotic cell. The host cell may further be a plant cell or a fungal cell. The plant cell may be from a tissue selected from the group consisting of: embryogenic plant tissue, organogenic plant tissue, vegetative plant tissue, callus tissue, and reproductive tissue. The plant cell may be a cell from a plant part selected from the group consisting of: pollen; ovule; immature plant embryo; mature plant embryo; seed; seedling; root; cotyledon; stem; node; internode; bud; leaf; shoot apical meristem; floral meristem; flower buds; inflorescence; and cultured plant material. As described above, the plant cell may be a dicotyledonous, monocotyledonous, or gymnosperm cell. The plant cell may be a soybean cell or a maize cell.

In other embodiments, a method of the invention may encompass a T-DNA comprising one or more plant expressible gene(s) of interest and/or regulatory gene(s) of interest. In other embodiments, a method of the invention may encompass a T-DNA comprising a nucleic acid molecule encoding for at least one genome editing nuclease. Any genome editing nucleases known in the art may be used, including but not limited to Zinc-finger nucleases (ZFNs), transcription activator-like effector nucleases (TALEN s), and clustered regularly interspaced short palindromic repeat (CRISPR)/Cas-based RNA-guided DNA endonucleases, such as Cas9 or Cpf1.

In other embodiments of a method of the invention, the step of contacting the *Agrobacterium* cell with the plant cell may be accomplished by at least one method selected from the group consisting of: incubating the plant cell, plant tissue, or plant with *Agrobacterium*; co-cultivation of the at least one plant host cell and the *Agrobacterium*; floral dip method; vacuum infiltration method; cotyledonary node method; and sonication-assisted *Agrobacterium*-mediated transformation. The step of contacting the *Agrobacterium* cell with the plant cell may also be accomplished by any combination of the methods listed above.

The present invention also encompasses a method of the invention described above, further comprising isolating or selecting for a host cell comprising the transgenic T-DNA. This is a transgenic host cell. The present invention also encompasses the transgenic cell produced by a method of the invention. The present invention also encompasses a transgenic plant produced by a method of the invention.

The present invention also embodies a nucleic acid molecule comprising a nucleic acid sequence at least 70%, 75%, 80%, 85%, 90%, 91%, 92%, 93%, 94%, 95%, 96%, 97%, 908%, 99%, or 100% identical to SEQ ID NO: 1, SEQ ID NO: 2, or SEQ ID NO: 3. In another embodiment, the present invention includes a disarmed pTiChry5 plasmid comprising a sequence at least 70%, 75%, 80%, 85%, 90%, 91%, 92%, 93%, 94%, 95%, 96%, 97%, 908%, 99%, or 100% identical to SEQ ID NO: 1, SEQ ID NO: 2, or SEQ ID NO: 3. All of these described nucleic acid molecules are not naturally occurring and are created by the hand of man, as described in Examples 2 and 3. The present invention also embodies a cell comprising these nucleic acid molecules.

The cell may be a eukaryotic or prokaryotic cell. The cell may be an *Agrobacterium* cell.

In other embodiments, an *Agrobacterium* strain or cell of the invention, for example *A. tumefaciens* strains Chry5d1, Chry5d2, and Chry5d3 are capable of introducing genome editing nucleases into a plant cell, plant tissue, or plant. In such embodiments, transgenic T-DNA contains one or more nuclease-encoding genes. Expressed in the plant cell, plant tissue, or plant, the genome editing nucleases aid in the insertion of a gene of interest or regulatory gene of interest, replace a native gene with a gene of interest or regulatory gene of interest, or remove or modify a native gene or native regulatory gene.

Preferably, the encoded nucleases are targeted to a specific position in the plant's genome. Introducing genome editing nucleases into a plant cell, plant tissue, or plant can provide for trait stacking, resulting in the physical linkage of certain traits to ensure co-segregation during breeding. In yet another preferred embodiment *A. tumefaciens* strains Chry5d1, Chry5d2, and Chry5d3 are further modified to increase transformation efficiency, such as by altering vir gene expression and/or induction thereof. This may be realized by the presence of mutant or chimeric virA or virG genes. Combinations with super-virulent plasmids are also possible, generating so-called super-virulent strains. Super-virulent strain variants may also be generated by employing pSBI or pVGW7 super virulence plasmid derived vectors.

The present invention also embodies a method for modifying a target site in the genome of a cell, comprising using an *Agrobacterium* strain or cell of the invention to introduce into the cell: (a) a first nucleic acid comprising at least 16 contiguous nucleotides, wherein the at least 16 contiguous nucleotides have at least 70%, 75%, 80%, 85%, 90%, 91%, 92%, 93%, 94%, 95%, 96%, 97%, 908%, 99%, or 100% identity with a target site in the genome of the cell, and further comprising a transgene; and (b) a second nucleic acid molecule comprising a nucleotide sequence encoding a nuclease for site-directed cleavage at a nuclease cleavage site in the genome of the cell adjacent to the nucleotide sequence in the genome of the cell that corresponds to the at least 16 contiguous nucleotides of (a), under conditions wherein expression of the second nucleic acid molecule can occur to produce the nuclease and the nuclease can cleave at the nuclease cleavage site in the genome of the cell and modify the target site in the genome of the cell.

Another embodiment of the present invention is a method of allelic replacement by targeted modification of a target genomic site in a cell, whereby the target genomic site comprises at least a fragment of a native gene, comprising using an *Agrobacterium* strain or cell of the invention to introduce into the cell: (a) a first nucleic acid molecule comprising a donor DNA molecule, which comprises at least 16 contiguous nucleotides at least 70%, 75%, 80%, 85%, 90%, 91%, 92%, 93%, 94%, 95%, 96%, 97%, 908%, 99%, or 100% identical to a genomic nucleic acid sequence, and further comprises a modified nucleic acid molecule comprising a nucleic acid sequence modified from the native gene; and (b) a second nucleic acid molecule comprising a nucleotide sequence encoding a nuclease for site-directed cleavage at a nuclease cleavage site in the genome of the cell adjacent to the nucleotide sequence in the genome of the cell that corresponds to the at least 16 contiguous nucleotides of (a), under conditions wherein expression of the second nucleic acid molecule can occur to produce the nuclease and the nuclease can cleave the nucleotide sequence at the target genomic site, whereby the modified nucleic acid molecule is integrated at the target genomic site in the genome of the cell.

In further embodiments of the methods described above, the first and/or the second nucleic acid molecule may be transiently expressed in the cell. In other embodiments, the cell may be a plant cell. Another embodiment of the present invention is a method of producing a genome modified plant, plant part, or progeny thereof, said method comprising regenerating a plant from the plant cell produced by the methods described above. Another embodiment of the invention is a genome modified plant, plant part, or progeny thereof, produced by the methods described above.

Particular embodiments are directed toward kits useful for the practice of one or more of the methods described herein. As used herein, a "kit" is any manufacture (e.g. a package or container) comprising at least one sample, e.g. a strain of *Agrobacterium*, for use in *Agrobacterium*-mediated transformation of a plant cell, plant tissue, or plant. In a particular embodiment, a kit comprises at least one aliquot or sample of an *Agrobacterium* strain of the invention, for example Chry5d1. Chry5d2, or Chry5d3. In another particular embodiment, the kit additionally comprises and at least one separate aliquot or sample comprising a binary plasmid, wherein the binary plasmid comprises a T-DNA region. In this embodiment, the T-DNA region of the binary plasmid preferably comprises right and left border sequences and minimal internal sequences. More preferably, the T-DNA region of the binary plasmid comprises no other T-DNA other than the right and left border sequences.

In another embodiment, the kit described herein further comprises additional elements, including but not limited to appropriate growth media, antibiotics useful for eliminating *Agrobacterium* following transformation, and a selection reagent capable of selecting for transgenic plant cells following transformation. In addition, the kits of the present invention may preferably contain instructions which describe a suitable detection assay. Such kits can be conveniently used, e.g., in laboratory settings, to transform plants with a gene of interest, regulatory gene of interest, selectable marker gene, reporter gene, or combinations thereof.

The kits described herein reduce the costs and time associated transforming a variety of plants, including Glycine ma (soybean). The kits may be used by research and commercial laboratories and agro-biotechnology companies to facilitate plant variety generation through *Agrobacterium*-mediated transformation.

The present invention will now be described with reference to the following examples. It should be appreciated that these examples are not intended to limit the scope of the claims to the invention, but are rather intended to be exemplary of certain embodiments. Any variations in the exemplified methods that occur to the skilled artisan are intended to fall within the scope of the present invention.

EXAMPLES

Example 1: Production of pTiChry5 Sequence

Attempts to return the fully disarmed pTiChry5, pTiKPSF2, to the Chry5 chromosomal background by electroporation of pTiKPSF2 into the cured Chry5C (Kovacs and Pueppke, 1993) were unsuccessful. Likewise, attempts to introduce pTiKPSF2 into a rifampicin resistant derivative of Chry5C by triparental mating with the mobilizer plasmid pRK2013 were not successful. These failed approaches indicate that the creation of a fully disarmed Chry5 strain is, in fact, not obvious. This is further supported by the fact that since the disclosure of the pTiKPSF2 plasmid in 2006 (Howe et al.), no reports have been made of a Chry5 strain comprising the fully disarmed pTiKPSF2 plasmid, despite the known ability of the Chry5 strain to efficiently transform dicots, including soybean (Bush and Pueppke. 1991), which is of very high economic importance.

Because these attempts were not successful, a disarmed pTiChry5 was created in situ, within the Chry5 strain, using homologous recombination. Surprisingly and unexpectedly, this strategy was successful and resulted in the production of three novel strains of Chry5, as described below.

To disarm Chry5 through homologous recombination, DNA sequence of pTiChry5 was needed. Genomes of several *Agrobacterium* strains have been fully sequenced, including *Agrobacterium tumefaciens* strain C58 (Goodner et al., 2001; Wood et al., 2001), *Agrobacterium radiobacter* K84 (Slater et al., 2009), *Agrobacterium vitis* S4 (Slater et al., 2009), and *Agrobacterium* sp. H13-3 (Wibberg el al., 2011). Additionally, sequences of multiple Ti plasmids, including the well-known pTiBo542, are also publicly available. The genome of Chry5 was sequenced and assembled using known *Agrobacterium* chromosome or Ti plasmid sequences as references.

Assembly of the Chry5 genome generated 61 scaffolds. Among them, scaffolds 57 (47,535 bp long) and 231 (176,318 bp long) exhibited good sequence alignment with pTiBo542 and were used to build pTiChry5. PCR was used to fill gaps between scaffold contigs (eight in scaffold 231 and two in scaffold 57) to orient and join scaffolds. The resulting assembly of the pTiChry5 plasmid is 224,731 nucleotides in length.

Example 2: Creation of Disarmed Chry5 Strains

TL-DNA and TR-DNA are located on pTiChry5 according to reported T-DNA border sequences (Palanichelvam et al., 2000). TL-DNA is about 13 Kb long and TR-DNA is about 10 Kb long. Primers were designed to PCR-amplify four DNA fragments (Fg1, Fg2, Fg3, and Fg4) flanking the two T-DNA regions (FIG. 1). Knockout vector constructs 20424, 20425 and 20426 were produced using these amplified fragments. Vector 20424 comprises Fg1 and Fg2, vector 20425 comprises Fg1 and Fg4, and vector 20426 comprises Fg2 and Fg3. These three vectors also comprise a gene encoding for resistance to the antibiotic spectinomycin and the sacB gene, which is useful for negative selection. The knockout vectors were introduced into Chry5 by electroporation or tri-parental mating. Integration of the vector by homologous recombination was selected for using spectinomycin. Homologous recombination for the removal of the vector backbone was negatively selected for by growing recombinants on solid media containing 5% sucrose. Construct 20424 was made to knock out both T-DNA regions and the ~18 Kb DNA sequence in between to create the fully disarmed strain Chry5d1. Constructs 20425 and 20426 were generated to sequentially knock out TL-DNA and TR-DNA in two steps to create the fully disarmed strain Chry5d2, which still carries the ~18 Kb DNA sequence between TL-DNA and TR-DNA on its disarmed Ti plasmid (FIG. 1).

Using vectors 20424, 20425, and 20426, four Chry5 strains (TL-DNA KO, TR-DNA KO, Chry5d1, and Chry5d2) were generated. Chry5d1 was generated using vector 20424. TL-DNA KO was generated using vector 20425. TR-DNA KO was generated using vector 20426. Chry5d2 was generated from TL-DNA KO by using vector 20426 to knock out TR-DNA. The strains were verified by PCR analysis. Primer pairs used to perform the PCRs are in Table 1. Targets Rx1 to Rx6 are pTiChry5 DNA regions located on pTiChry5 outside of the T-DNA regions. TL-DNA Rx(and TL-DNA Rx10 are on the TL-DNA. TL-DNA border (L), TL-DNA border (R), and TR-DNA border (L) are DNA regions across a the indicated T-DNA border, with one primer located on the T-DNA and the other primer located outside of the T-DNA. ΔTL-DNA, ΔTR-DNA, and ΔTL-R-DNA indicate the disarmed strains. Results of the PCRs are shown in Table 2. This analysis confirms that pTiChry5d2 has the TL region (13.4 Kb) deleted from TL-RB to the 1st LB (internal LB) of the TL.

TABLE 1

PCR primer pairs used to verify disarmed pTiChry5 plasmids

| Target/Purpose | SEQ ID NO. | Sequence |
|---|---|---|
| Rx1: TR right border position 1 (TR1) | 4 | GTCTGACCGTCCCACCAAAGAAG |
|  | 5 | GGGATCCGCTTCAACACAAGTCC |
| Rx2: entire T-DNA region | 6 | GCCGCGAAGGCGAGTTCC |
|  | 7 | GCTCGAGGCCGTACCAACTG |
| Rx3 | 8 | CGGCATGGCACCGTCGAG |
|  | 9 | GTGCATCGCTGGTGGGCAAG |
| Rx4 | 10 | CATGCGGTAGTTGACGATACGG |
|  | 11 | ATCCAGCTCAAGTCGCATCCAAC |
| Rx5: pTiChry5 intactness outside of T-DNA region (T) | 12 | CTCCGCTTACAACACCGGTAATTTC |
|  | 13 | CACCGCACAAGCTTGGGGC |
| Rx6 | 14 | GGCACCAGATCGGCATGATCG |
|  | 15 | CAGGCCAATCCACCCTTCCTACC |
| Rx9: TL-DNA | 16 | AACATGATGCCGTATGACTTTCTCTTC |
|  | 17 | ATGACTCAGCAACCTACTATCCCG |
| Rx10: TL2 | 18 | GATAAAATTGAGGTCTTCCTGTTTGGAGC |
|  | 19 | GCAGTGCTAGAGCGTTCACG |
| C1: Chry5-specific chromosome position 1 | 20 | AGTGGTCTTGATGACGGCGT |
|  | 21 | GCGTCGGGTTCCGCCATA |
| C2: Chry5-specific chromosome position 2 | 22 | CACCGGGCCGCACTTTTG |
|  | 23 | GCCAGAGAAAACGAACGTATCATTA |
| TL1 | 24 | CGACAGGTGGGCCAGTAGCATTAC |
|  | 25 | CGCCGGTCTTGTAGATTCGAGC |
| TL-DNA border (R) | 26 | CCATGGCGCAGCTTCGAGG |
|  | 27 | CGCATTGATTGCTTGGGTAGAGC |
| TR-DNA border (L) | 28 | CGCGAAATGAGCGCCTAAAGTTC |
|  | 29 | GCGGGAATAGCGACCGAAGGC |
| ΔTL-DNA | 24 | CGACAGGTGGGCCAGTAGCATTAC |
|  | 26 | CCATGGCGCAGCTTCGAGG |
| ΔTR-DNA | 24 | GCTGGAGGAGACCGCGGTGAC |
|  | 29 | GCGGGAATAGCGACCGAAGGC |
| ΔTL-R-DNA | 24 | CGACAGGTGGGCCAGTAGCAT |
|  | 30 | GCTGGAGGAGACCGCGGTGAC |

TABLE 2

Verification of disarmed Chry5d1 and Chry5d2 by PCR analysis

| Target | Chry5 wt | TL-DNA KO | TR-DNA KO | Chry5d2 | Chry5d1 |
|---|---|---|---|---|---|
| C1 | Y | Y | Y | Y | Y |
| C2 | Y | Y | Y | Y | Y |
| Rx1 | Y | Y | Y | Y | Y |
| Rx2 | Y | Y | Y | Y | Y |
| Rx3 | Y | Y | Y | Y | Y |
| Rx4 | Y | Y | Y | Y | Y |
| Rx5 | Y | Y | Y | Y | Y |
| Rx6 | Y | Y | Y | Y | Y |
| Rx9 | Y |  | Y |  |  |
| Rx10 | Y |  | Y |  |  |
| ΔTL-DNA |  | Y |  |  | Y |
| ΔTR-DNA |  |  | Y |  | Y |
| TL-DNA border (L) | Y |  | Y |  |  |
| TL-DNA border (R) | Y |  | Y |  |  |
| TR-DNA border (L) | Y | Y |  |  | Y |
| ΔTL-R-DNA |  |  |  |  | Y |

Example 3: Creation of Chry5d3 Strain

Vector construct 22535 was used to disarm the Chry5 wild-type strain following a strategy similar to Example 2. Vector 22535 was designed with the flanking fragments (Fg5 and Fg6) to generate pTiChry5d3, a fully disarmed derivative of pTiChry5 with a deletion of 56,645 bp including the entire T-DNA region and several possible transposon elements. Following selection using spectinomycin and sacB counter-selection, the putative Chry5d3 strain was verified by PCR-based analysis (Tables 3 and 4), similar to what is described in Example 2. Compared to pTiChry5d2, pTiChry5d3 has a larger deletion to remove the whole TL region (15.7 Kb) that includes the 2.3 Kb sequence from the internal LB to TL-LB.

Patent Application Publication Nos. 20070004912, 20050246798, and 20050060767). These vectors were electroporated into *Agrobacterium* strains Chry5d2 and EHA101 using methods well-known in the art. Soybean transformation was performed and transformants were selected and regenerated using glyphosate, as described in U.S. Patent Publication US2016/0186200 (incorporated by reference herein). TAQMAN™ qPCR was used to determine copy

TABLE 3

Primers used for verification of disarmed pTiChry5d3 by PCR analysis

| Target/Purpose | SEQ ID NO. | 5'-PrimerSequence-3' |
|---|---|---|
| C1: Chry5-specific chromosome position 1 | 20 | AGTGGTCTTGATGACGGCGT |
|  | 21 | GCGTCGGGTTCCGCCATA |
| C2: Chry5-specific chromosome position 2 | 22 | CACCGGGCCGCACTTTTG |
|  | 23 | GCCAGAGAAAACGAACGTATCATTA |
| T: pTiChry5 intactness outside of T-DNA region | 12 | CTCCGCTTACAACACCGGTAATTTC |
|  | 13 | CACCGCACAAGCTTGGGGC |
| TL1: TL left border position 1 | 24 | CGACAGGTGGGCCAGTAGCATTAC |
|  | 25 | CGCCGGTCTTGTAGATTCGAGC |
| TL2: TL right border position 2 | 18 | GATAAAATTGAGGTCTTCCTGTTTGGAGC |
|  | 19 | GCAGTGCTAGAGCGTTCACG |
| TR1: TR right border position 1 | 4 | GTCTGACCGTCCCACCAAAGAAG |
|  | 5 | GGGATCCGCTTCAACACAAGTCC |
| TR2: TR right border position 2 | 31 | GCAAGCCGAGATGCAGTAAGGC |
|  | 32 | CGAGAACCGTCGGATCGTTGGC |
| J1: Deletion scar joint fragment 1 | 33 | GATGTACTGCGGAAAAATCGTCGAG |
|  | 34 | CTTTGGTCACGCCCGTCCTATC |
| J2: Deletion scar joint fragment 2 | 35 | GGCGAGTCTGGTTGTGGAAAAAGC |
|  | 31 | GCAAGCCGAGATGCAGTAAGGC |

TABLE 4

Verification of disarmed Chry5d3 by PCR analysis

| Target | Chry5 wt | Chry5d3 |
|---|---|---|
| C1 | Y | Y |
| C2 | Y | Y |
| T | Y | Y |
| TL1 | Y | N |
| TL2 | Y | N |
| TR1 | Y | N |
| TR2 | Y | N |
| J1 | N | Y |
| J2 | N | Y |

Example 4: Chry5d2 and Chry5d3 Outperform EHA101 for Soybean Transformation

*Agrobacterium* strain EHA101 (Hood et al., 1986, J. Bacteriology 168: 1291-1301) is used routinely for soybean transformation. Strains Chry5d2 and EHA101 were compared for soybean transformation efficiency by using three binary vectors: 20285, 21028 and 21095. The T-DNA for 21095 comprises a single expression cassette, and is ~4.05 kB. The T-DNAs for 20285 and 21028 each comprises two expression cassettes; 20285 is ~10.9 kB and 21028 is ~9.4 kB. All three comprise a nucleic acid sequence encoding for 5-enol-pyrovyl-shikimate-3-phosphate-synthase (EPSPS) gene, which allows for transformant selection using glyphosate (Castle et al. 2004, Science 304:1151-1154, and U.S.

number of the introduced genes and to determine the presence of binary vector backbone. TAQMAN™ assays were performed following standard methodology using JumpStart™ Taq ReadyMix™ (Sigma-Aldrich) and the ABI PRISM® 7900HT sequence detection system. Events were considered low-copy, meaning they were likely to have only one copy of the introduced sequence, if they had a raw TAQMAN™ copy number value of 0.3 to 1.3. Events with a raw TAQMAN™ number above 1.3 were considered medium to high copy number, and are believed to contain more than one copy of the EPSPS gene or other genes of interest within the T-DNA. Events were considered backbone free if the raw TAQMAN™ copy number was 0. Transformation frequency is calculated as the percentage of transgenic events for a given construct with a given number of transformation explants used for the transformation. For example, if 100 soybean explants were initially transformed, and it was eventually determined that 5 of the events contained full or part of the T-DNA, the transformation frequency (TF %) would be 5%.

Table 5 shows the percentage of low copy events (LC %; events with single copy of gene of interest integrated/total transgenic events), and backbone free (BB free %; events backbone free/total transgenic events) based on the results of the TAQMAN™ analysis, and the calculated transformation frequency (TF %) for each of the given constructs, Chry5d2 consistently exhibited higher TF (>50% increase) and low copy frequency. It is known in the art that *Agrobacterium* strains may have different performance levels on different cultivars of the same plant species, especially if that species is recalcitrant to transformation. It is known that a modified Chry5 strain is supervirulent on the soybean cultivar Peking (Bush and Pueppke, 1991). These results indicate that the Chry5 supervirulence may not be limited to specific cultivars. Additionally, no disease symptoms were observed on transformants generated with the Chry5d2 strain. Finally, the results here show that a large T-DNA of over 10 kB can successfully be transferred into soybean at a high transformation efficiency using Chry5d2. Therefore, the Chry5d2 strain is disarmed, non-tumorgenic, and retains supervirulence on soybean. Such a Chry5 strain has not been described previously, despite a need in the art for highly virulent *Agrobacterium* strains on soybean.

TABLE 5

Chry5d2 outperforms EHA101 on Soybean cv Jack

| Strain | Vector | Events | TF (%) | LC (%) | BB Free (%) |
|---|---|---|---|---|---|
| EHA101 | 20285 | 12 | 1.66 | 41.67 | 66.67 |
| Chry5d2 | 20285 | 28 | 3.86 | 60.71 | 85.71 |
| EHA101 | 21028 | 62 | 8.31 | 75.81 | 87.1 |
| Chry5d2 | 21028 | 87 | 12.72 | 81.61 | 88.51 |
| EHA101 | 21095 | 69 | 10.13 | 69.57 | 76.81 |
| Chry5d2 | 21095 | 119 | 17.66 | 73.95 | 74.79 |

A further analysis was performed which included the Chry5d3 strain. Three different binary vectors (21028, 21095 and 21365) with EPSPS as selectable marker gene were electroporated into different disarmed *Agrobacterium* strains (EHA101, EHA101 recA−, Chry5d2, Chry5d2 recA− and Chry5d3 recA−). Chry5d2 and Chry5d3 strains were modified to become recA− strains using vector 20689 and methods well-known in the art. Vector 20689 comprises 5' and 3' flanking sequences to the Chry5 recA gene. 20689 also comprises a bom site useful for tri-parental mating. As a result of homologous recombination, the recA gene was removed from the bacterial chromosome of Chry5d2 and Chry5d3. The generated Chry5d2 recA− and Chry5d3 recA− strains were verified by a PCR-based method similar to that of Example 2. Binary vector 21365 comprises a very large T-DNA of ~17.6 kB. Binary vectors were introduced into the *Agrobacterium* strains and transformed into soybean using the same methods as described above. Events were selected for and regenerated using glyphosate following the same methods as described above.

Results are shown in Table 6. The number of examples inoculated with the *Agrobacterium* strain is indicated (# explants), as is the number of events identified by TAQMAN assay (Events) and the transformation efficiency (TF %). All fully disarmed Chry5 strains, either recA+ or recA−, outperformed EHA101 and EHA101 recA−. This data indicates that the disarmed Chry5d2 and Chry5d3 strains are capable of transformation of plants with very large T-DNAs at high frequency.

TABLE 6

Chry5d2 and Chry5d3 outperform EHA101 on soybean cv Jack

| Strain | Vector | # Explants | Events | TF (%) |
|---|---|---|---|---|
| EHA101 | 21028 | 791 | 97 | 12.3% |
| Chry5d2 | 21028 | 774 | 119 | 15.4% |
| EHA101 | 21095 | 1351 | 173 | 12.8% |
| EHA101 recA− | 21095 | 1194 | 131 | 11.0% |
| Chry5d2 | 21095 | 739 | 120 | 16.2% |

TABLE 6-continued

Chry5d2 and Chry5d3 outperform EHA101 on soybean cv Jack

| Strain | Vector | # Explants | Events | TF (%) |
|---|---|---|---|---|
| EHA101 recA− | 21365 | 264 | 44 | 16.7% |
| SYT101 recA− | 21365 | 257 | 48 | 18.7% |
| Chry5d2 recA− | 21365 | 206 | 54 | 26.2% |
| Chry5d3 recA− | 21365 | 291 | 73 | 25.1% |

Example 5: Chry5d2 Capable of Transformation of Monocots

It is well-known in the art that monocotyledonous plants are more difficult to transform via *Agrobacterium*-mediated transformation, so that direct DNA transfer methods such as electroporation and particle gun transformation have been more widely used. However, direct DNA transfer methods suffer deficiencies, including frequent incorporation of the DNA into the host genome and multiple copies of the desired gene rearranged with flanking sequences from the plasmid vector inserted into the host genome. These rearrangement and integration events may result in gene expression that is aberrant and unstable in the transformed plant and its progeny. Therefore, Chry5d3 was assayed to determine its ability to transform monocot plants.

Example 5.1: Transformation of Corn

*Agrobacterium* strain LBA4404 is a disarmed strain with the Ach5 background (Ooms et al., 1982, Plasmid 7: 15-29). LBA4404 is routinely used for plant transformation and is readily commercially available, for example from Thermo Fisher Scientific (Catalog No. 18313015). In these examples, LBA4404 recA− comprises the helper plasmid 17740 (pVGW7; U.S. Patent Application Publication US2016/0083737). Binary vector 12672, which comprises a T-DNA of ~7.1 kB that contains two expression cassettes, was used. The first expression cassette encodes for the AmCyan fluorescent protein (CFP) gene under the control of maize ubiquitin-1 promoter, and the second expression cassette encodes for PMI (phosphomannose-isomerase) as a selectable marker gene (U.S. Pat. Nos. 5,767,378 and 5,994,629) under the control of maize Ubi-1 promoter (Sivamani et al., 2015, Transgenic Res 24:1017-1027, hereby incorporated by reference in its entirety). Binary vector 12672 was introduced into disarmed *Agrobacterium* strains EHA101, Chry5d2, and LBA4404 recA−(17740)) by electroporation. Individual *Agrobacterium* strains were used to transform maize immature embryo explants, and mannose selection was used to identify and regenerate transgenic plants (Sivamani et al., 2015). Table 7 shows transformation frequency of side-by-side comparison experiments. All fully disarmed Chry5d2 strains outperform EHA101. This data indicates that the fully disarmed Chry5d2 is capable of infecting and transforming maize.

TABLE 7

Chry5d2 can transform maize

| Strain | # Explants | Events | TF (%) |
|---|---|---|---|
| EHA101 | 963 | 111 | 11.5% |
| Chry5d2 | 1312 | 287 | 21.9% |
| LBA4404 recA− (17740) | 1104 | 330 | 29.9% |

Example 52: Chry5d2 Generates High Quality Sugarcane Transgenic Events

Binary vector 21745 with PMI as selectable marker gene was introduced into disarmed *Agrobacterium* strains LBA4404 recA– (17740), EHA101 recA– (17740) and Chry5d2 recA– (17740)) by electroporation. 21745 has a very large T-DNA of ~28.2 kB, comprising four expression cassettes. Individual *Agrobacterium* strains were used to transform sugarcane callus explants as described before using mannose selection (Dong et al., 2014. Advances in *Agrobacterium*-Mediated Sugarcane Transformation and Stable Transgene Expression. Sugar Tech. 16:366-371, herein incorporated by reference in its entirety).

Table 8 below shows transformation frequency of side-by-side comparison experiments. For sugarcane, the total grams of callus explants inoculated is shown, followed by the number of positive events as determined by TAQMAN analysis of the PMI gene. Transformation frequence (TF) is calculated as the number of events per gram of starting callus tissue. The fully disarmed Chry5d2 recA– (17740) strain outperforms LBA4404 recA– (17740). This indicates that Chry5d2 is also suitable for transformation of sugarcane. EHA101 recA– (17740) resulted in the highest transformation frequency in this set of experiments. However, further analysis showed that a higher percentage (15.1%) of transgenic events from the Chry5d2 recA– (17740) strain had low copy, backbone-free events compared to similar events from EHA101 recA– (17740) (9.5%). Therefore, the Chry5d2 strain has high efficiency in generating high quality transgenic events of very large T-DNA insertions.

TABLE 8

Chry5d2 is capable of transforming sugarcane

| Strain | Callus explant (g) | Events | TF (%) |
|---|---|---|---|
| LBA4404 recA- (17740) | 45 | 15 | 0.3 |
| EHA101 recA- (17740) | 45 | 336 | 7.5 |
| Chry5d2 recA- (17740) | 45 | 252 | 5.6 |

Example 53: Transformation of Wheat

In a total of 16 wheat transformation experiments using cultivar Fielder, Chry5d2 was compared with EHA101 using binary construct 18515, which comprises the PMI selection marker and the AmCyan reporter gene. Transient expression of Amcyan was monitored under florescence microscope at three to four days after *Agrobacterium* infection. Although distribution of CFP spots on infected embryos was similar for both treatments, slightly less CFP spot number and overall CFP intensity were observed on Chry5d2-infected embryos compared to those infected by EHA101. Consistently, EHA101 outperformed Chry5d2 with regard to TF. However, the transformation experiments using Cry5d2 reproducibly showed increased frequency of low copy and backbone-free events (Table 9).

TABLE 9

Chry5d2 generates high quality wheat transgenic events

| Strain | Events | TF (%) | LC (%) | BB free (%) |
|---|---|---|---|---|
| EHA101 | 180 | 23.2 | 38.89 | 47.67 |
| Chry5d2 | 108 | 12.2 | 65.74 | 69.44 |

Chry5d2 also transformed other wheat cultivars including 03S0352-22 and Knudson. This shows that Chry5d2 retains the highly desirable virulent qualities of Chry5, even on monocots, especially on monocots recalcitrant to transformation such as wheat and sugarcane, but is not tumorigenic because of the engineered disarmed pTiCry5d2 plasmid. It is expected that strains Chry5d1 and Chry5d3 would provide similar results.

Example 6: Transient Assays

In the following example, Chry5d2 and Chry5d3 were successfully used for transient assays in the dicot plant tobacco, the monocot plant maize, and in sugarcane, which is known to be recalcitrant to transformation. Binary vector 12672 was used for tobacco and maize transient assay experiments. 12672 was introduced by eletroporation into the following *Agrobacterium* strains with or without additional helper plasmid 17740: LBA4404 recA–, LBA4404 recA– (17740), EHA101 recA–, EHA101 recA– (17740), Chry5d2, Chry5d2(17740), Chry5d2 recA–, Chry5d2 recA– (17740), Chry5d3 recA– and Chry5d3 recA–(17740). The resulting strains carrying binary vector 12672 were individually cultured and infiltrated into tobacco (Table 10), maize (Table 11) or sugarcane (Table 12) leaves essentially as described (U.S. Pat. No. 8,642,839, incorporated in its entirety herein). Leaf disc samples were collected from leaves of two infiltrated plants. PMI and AmCyanFP (CFP) protein levels in the collected leaf samples were determined using quantitative ELISA assays following methods known in the art. Results showing the amounts of PMI and CFP protein detected are shown in the Tables below. It will be appreciated that the presence of the protein indicates successful delivery of the T-DNA encoding the PMI and CFP gene to the plant cell and successful transcription and translation of PMI and CFP proteins.

TABLE 10

PMI and CFP protein levels in tobacco transient assays

| Strain | PMI level (ng/mg TSP) | CFP level (ng/mg TSP) |
|---|---|---|
| LBA4404ecA- | 0.22 +/- 0.08 | 0 |
| LBA4404 recA- (17740) | 0.21 +/- 0.04 | 0 |
| EHA101 recA- | 1.27 +/- 0.15 | 0.34 +/- 0.10 |
| EHA101 recA- (17740) | 1.04 +/- 0.19 | 0.27 +/- 0.16 |
| Chry5d2 | 0.91 +/- 0.57 | 0.13 +/- 0.06 |
| Chry5d2 (17740) | 0.62 +/- 0.25 | 0.10 +/- 0.02 |
| Chry5d2 recA- | 1.02 +/- 0.29 | 0.12 +/- 0.03 |
| Chry5d2 recA- (17740) | 0.55 +/- 0.22 | 0.07 +/- 0.02 |
| Chry5d3 recA- | 2.10 +/- 0.73 | 0.62 +/- 0.80 |
| Chry5d3 recA- (17740) | 1.12 +/- 0.20 | 0.18 +/- 0.07 |

TABLE 11

PMI and CFP protein levels in maize transient assays

| Strain | PMI level (ng/mg TSP) | CFP level (ng/mg TSP) |
|---|---|---|
| LBA4404 recA- | 0 | 0.15 +/- 0.03 |
| LBA4404 recA- (17740) | 0 | 0.14 +/- 0.06 |
| EHA101 recA- | 0.23 +/- 0.11 | 2.62 +/- 1.90 |
| EHA101 recA- (17740) | 0.16 +/- 0.07 | 1.69 +/- 1.32 |
| Chry5d2 | 0.22 +/- 0.05 | 2.71 +/- 1.10 |
| Chry5d2 (17740) | 0.84 +/- 1.14 | 1.18 +/- 0.90 |
| Chry5d2 recA- | 0.45 +/- 0.21 | 4.71 +/- 3.24 |
| Chry5d2 recA- (17740) | 0.15 +/- 0.05 | 1.54 +/- 0.90 |
| Chry5d3 recA- | 0.19 +/- 0.05 | 3.12 +/- 2.12 |
| Chry5d3 recA- (17740) | 0.14 +/- 0.05 | 1.05 +/- 0.36 |

Binary vector 21578 was used for sugarcane transient assays. Binary vector 21578 comprises two expression cassettes, one of which encodes for the AmCyan (CFP) protein and the second which encodes for the GUS (β-glucuronidase) protein. The binary vector 21578 was introduced into two *Agrobacterium* strains, namely EHA101 and Chry5d2, and infiltrated into attached sugarcane leaves following the methods described in U.S. Pat. No. 8,642,839.

TABLE 12

GUS and CFP protein levels in sugarcane transient assays

| Strain | GUS protein level (ng/mg TSP) | CFP protein level (ng/mg TSP) |
|---|---|---|
| EHA101 | 16.14 ± 13.86 | 16.82 ± 11.97 |
| Chry5d2 | 38.02 ± 34.88 | 21.62 ± 19.00 |

The transient expression level of PMI and CFP genes as suggested by their protein content in the infiltrated tobacco (Table 10) and maize (Table 11) leaf samples were highest when Chry5d2 recA– or Chry5d3 recA– strains were used. In particular, Chry5d2 recA– or Chry5d3 recA– strains resulted in significantly higher CFP protein levels in infiltrated maize leaf samples. LBA4404 recA– strains with or without 17740 helper had the lowest protein expression level in both tobacco and maize leaf samples. It is unexpected that strains containing helper plasmid 17740 resulted in significantly lower PMI and CFP protein content than the strains without the helper plasmid in both infiltrated tobacco and maize leaf samples. Infiltration results in sugarcane leaves also suggest that Chry5d2 strain was performing favorably in comparison with EHA101 (Table 12). Because of the difficulty in infiltrating sugarcane leaves, there was a large variation in the results as indicated by the large standard deviation. Regardless, these data clearly show that the fully disarmed Chry5d2 and Chry5d3 strains may be used for transient assays of plants, including plants typically recalcitrant to transformation, and further provide improvement over other *Agrobacterium* strains typically used. The Chry5d1 strain, which is similarly disarmed, could also be used in similar methods.

Example 7: Use of Chry5d2 for Targeted Transgene Insertion

The application of site-directed nucleases (SDNs)-mediated targeted insertion technology for trait improvement has been demonstrated in several field crops, including tobacco (Cai et al, 2009. Plant Mol Biol, 69:699-709), cotton (Dhalluin et al, 2013. Plant Biotechnology Journal, 11: 933-941) and maize (Dhalluin et al, 2008. Plant Biotechnology Journal, 6: 93-102; Ainley et al, 2013. Plant Biotechnology Journal, 11: 1126-1134). Significant advances have been made in the last few years towards the development of methods and compositions to target and cleave genomic DNA by site specific nucleases (e.g., Zinc Finger Nucleases (ZFNs), Meganucleases, Transcription Activator-Like Effector Nucleases (TALENS) and Clustered Regularly Interspaced Short Palindromic Repeats/CRISPR-associated nuclease (CRISPR/Cas) with an engineered crRNA/tracr RNA), to induce targeted mutagenesis, induce targeted deletions of DNA sequences, and facilitate targeted recombination of an exogenous donor DNA polynucleotide, such as a transgene, within a predetermined genomic locus.

Successful insertion of an exogenous donor DNA polynucleotide molecule to a targeted genomic locus remains difficult, however. A high percentage of these targeted insertion events contain at least one end repaired by the Non-Homologous End Joining (NHEJ) process, which allows for the insertion of multiple donor DNA fragments in multiple orientations and does not result in a predictable junction sequence connecting these donor DNA fragments with the target locus. The low frequency of precise targeted insertion generated by double crossover homologous recombination (HR) remains to hinder the full deployment of the technology in a routine event generation pipeline. Therefore, there is a need in the art to develop methods that increase targeted insertion, both for trangene insertion and for allelic replacement via recombination. A method which improves the transformation frequency of the nucleic acid molecules encoding the nuclease and/or the donor nucleic acid molecule would significantly impact the number of successful events recovered. As described in the present application, the novel *A. tumefaciens* Chry5d strains developed herein significantly increase transformation frequency of tested plants. Therefore, the following expression cassettes were constructed and introduced into Chry5d strains for use in plant transformation and further for use in targeted transgene insertion. It is recognized that similar approaches could be used for targeted genomic modifications, such as gene or allele replacement.

Example 7.1: Construction of Expression Cassettes for Maize Targeted Transgene Insertion A pair of heterodimeric TALEN genes was designed to cleave target sequences MIR604FR3 (5'-TCCGT GCAGT GCAGT GCAGT GCAGG ACAGG ACCTC CTTTG TTTAG GA-3', SEQ ID No.19) located within the MIR604 transgene insertion site as described in patent publication WO16033230, herein incorporated by reference. One of the TALEN genes, cTNmir604Fw3-01 (SEQ ID No. 20) encodes a TALEN protein TLNmir604S3Fw (SEQ ID No. 21) recognizing target sequence "tCCG TGC AGT GCA GTG T" (SEQ ID No. 22). The other, cTNmir604Rv3-01 (SEQ ID No. 23), encodes a TALEN protein TLNmir604S3Rv (SEQ ID No. 24) recognizing DNA sequence "tCCT AAA CAA AGG AGG T" (SEQ ID No. 25). Binary vector 23404 comprising expression cassettes comprising this pair of TALEN genes was produced using conventional gene synthesis and cloning methods.

Targeted insertion donor vector 22445 comprises three expression cassettes, two of which comprise coding sequences for two different trait genes, and the third which comprises the PMI selectable marker gene. All three expression cassettes are between two homology arms: xJHAX-03 (SEQ ID No. 6) and xJHAX-04 (SEQ ID No. 7). From the 5' end, the donor nucleic acid sequence comprises xJHAX-03 linked to the two trait gene expression cassettes in tandem, linked to the PMI expression cassette, which is linked to xJHAX-04. The two homology arms (xJHAX-03 and xJHAX-04) have sequences identical to part of the MIR604 insertion site sequences as taught in patent publication WO16033230 and are for guiding the targeted insertion of the donor sequences to the TALEN cleavage site at the target locus using homologous recombination. In the targeted insertion experiments described below, transformation was carried out using *Agrobacterium*-mediated gene delivery and immature embryos as target explants. Other tissues or explants such as cultured immature embryos or calli derived from cultured embryos or shoots or leaf rolls can also be used as transformation target materials.

Example 7.2: Generation of Targeted Insertion Events at the MIR604 Insertion Site Locus with *Agrobacterium*-Mediated Transformation Elite maize transformation variety NP2222 (U.S. Pat. No. 6,710,233, incorporated by references in its entirety herein) was chosen for all experiments. Methods for *Agrobacterium*-mediated transformation, callus induction and selection, plant regeneration and rooting have been described previously (Negrotto et al., 2000, Plant Cell Reports 19:798-803; Ishida et al., 1996, Nat. Biotechnol. 14:745-750). Briefly, a suspension comprising an *Agrobacterium* strain comprising TALEN expression vector 23404 was mixed with a suspension comprising an *Agrobacterium* strain comprising donor expression cassette 22445. The mixed suspension was then used for infection of immature embryos of NP2222. After infection, immature embryos were co-cultivated for 2-3 days and then moved to callus induction medium for 10-14 days followed by transfer of calli to mannose selection media. Mannose resistant calli were selected and transferred to regeneration media for shoot formation. Shoots were then sub-cultured onto rooting media. Samples were then harvested from rooted plants for Taqman assays to detect mutations in the target site to enrich for potential targeted insertion events; subsequent junction PCR analyses were performed to identify events putatively containing the targeted insertion, as described in WO16033230 (incorporated by reference in its entirety herein). Identified putative targeted insertion events were further characterized by additional PCR, sequencing and Southern analysis for confirmation of the targeted insertion using standard methods well-known in the art.

Table 12 summarizes the results from comparison experiments using different *Agrobacterium* strains to co-deliver TALEN and donor DNA for targeted insertion of donor sequence into the target sequence MIR604FR3 at the maize genomic locus MIR604 insertion site. The results in Table 12 show significant improvement of targeted insertion frequency when *Agrobacterium* strain Chy5d2 recA–(17740) was used to deliver both TALEN expression and donor vectors. The use of *Agrobacterium* strain Chy5d2 recA–(17740) to co-deliver both TALEN and donor binary vectors out-performed all other combination of *Agrobacterium* strains tested, and is able to produce a total of 12 targeted insertion events, at a targeted insertion frequency of 0.72%. Among the 12 targeted insertion events, 6 were identified to be products of double crossover homologous recombination (HR) at both homology arms. The high quality double crossover targeted insertion frequency is increased to 0.36%, meaning more than 3 targeted transgene insertion events could be generated from 1000 immature embryos. On the contrary, high quality double crossover targeted insertion frequency is only 0.05% when other *Agrobacterium* strains LBA or EHA were used (Table 3.

TABLE 13

Targeted insertion efficiency from different Agrobacterium strains

| Expt | Strains vector 23404 | Strains vector 22445 | Total No. of embryos | Total transgenic events | Events with target site mutation | Events with confirmed targeted insertion NHEJ | Events with confirmed targeted insertion HR | Targeted insertion frequency HR | Targeted insertion frequency Total (NHEJ + HR) |
|---|---|---|---|---|---|---|---|---|---|
| A | LBA | LBA | 5820 | 1034 | 99 | 1 | 1 | 0.02% | 0.03% |
| B | LBA | Chry | 1500 | 301 | 40 | 2 | 1 | 0.07% | 0.20% |
| C | LBA | EHA | 1845 | 145 | 31 | 0 | 1 | 0.05% | 0.05% |
| D | Chry | LBA | 2545 | 370 | 92 | 2 | 1 | 0.04% | 0.12% |
| E | Chry | Chry | 1665 | 423 | 141 | 6 | 6 | 0.36% | 0.72% |
| F | EHA | LBA | 2560 | 478 | 27 | 1 | 0 | 0.00% | 0.04% |
| G | EHA | EHA | 2340 | 99 | 14 | 2 | 0 | 0.00% | 0.09% |

To compare the effectiveness of co-delivery of both donor and TALEN nuclease DNA using different combinations of *Agrobacterium* strains, the presence of mutations in all transgenic events listed in Table 12 was assayed by Taqman assays (Table 13). The total number of events comprising the donor nucleic acid molecule PMI was used to evaluate transformation efficiency of the combination of *Agrobacterium* strains in co-delivery of TALEN expression vector 23404 and donor vector 22445. Highest transformation efficiency (25.4%) was achieved by the combination of Chry5d2 (23404)/Chry5d2 (22445), followed by LBA4404 (23404)/Chry5d2 (22445) (20.1%), EHA101 (23404)/LBA4404 (22445) (18.7%), LBA4404 (23040)/LBA4404 (22445) (17.8%), Chry5d2 (23404)/LBA4404 (22445) (14.5%), LBA4404 (23404)/EHA101 (22445) (7.9%), and EHA101 (23404)/EHA101 (22445) (4.2%), meaning that the strain Chry5d2 have is most effective in delivering donor nucleic acid into plant cells followed by LBA4404 and EHA101 (Table 4). The combination of Chry5d2 (23404)/Chry5d2 (22445) also generated the highest percentage (23.4%) of events with larger sequence deletion which is indicative of potential sequence replacement and targeted insertion, followed by other combinations tested. This trend is also observed in the frequency of co-integration of both donor nucleic acid and TALEN in transgene events (Table 14).

Effects of the combination of *Agrobacterium* strains on TALEN activities in plant cell are analyzed. When using Chry5d2 to infect the immature embryos of elite line NP2222, up to 33.3% of events generated positive for integration of donor nucleic acid have their target site (MIR604FR3) modified either in one allele (33.3%, 47 out of 141 events) or both alleles (66.7%, 94 out of 141 events) of the maize genome. In comparison of the combination of *Agrobacterium* strain Chry5d2, other combination of *Agrobacterium* strains tested generated much low percentages of PMI events having their target site (MIR604FR3) modified, which are 24.9% (Chry5d2 (23404)/LBA4404 (22445)), 9.6% (LBA4404 (23040)/LBA4404 (22445)), 13.3% (LBA4404 (23404)/Chry5d2 (22445)), 21.4% (LBA4404 (23404)/EHA101 (22445)), 5.6% (EHA101 (23404)/LBA4404 (22445)), and 14.1% (EHA101 (23404)/EHA101 (22445)). This result also shows the Chry5d2 out-performed the other *Agrobacterium* strains LBA4404 and EHA101 in delivering effective TALEN into plant cells. It is reasonable to expect that similar results would be obtained using Chry5d1 or Chry5d3 for plant transformation.

TABLE 14

Analysis of different types of events in regenerated plants targeted at the MIR604 insertion site target sequence MIR604FR3 using different Agrobacterium strains to delivery nuclease and donor DNA

| TREATMENT | A | B | C | D | E | F | G |
|---|---|---|---|---|---|---|---|
| Total immature embryo targets | 5820 | 1500 | 1845 | 2545 | 1665 | 2560 | 2340 |
| Total regenerated events | 1215 | 369 | 177 | 589 | 475 | 664 | 120 |
| Donor (PMI) positive events (Transformants) | 1034 | 301 | 145 | 370 | 423 | 478 | 99 |
| 3.0 Transformation Frequency | 17.8% | 20.1% | 7.9% | 14.5% | 25.4% | 18.7% | 4.2% |
| 3.1 PMI positive events with co-integration of TALEN vector | 44 | 31 | 27 | 58 | 116 | 6 | 5 |
| Percentage | 4.5% | 10.3% | 18.6% | 15.7% | 27.4% | 1.3% | 5.1% |
| 3.1.1 PMI positive events with no target site modification | 935 | 261 | 114 | 278 | 282 | 451 | 85 |
| 3.1.2 PMI positive events with larger sequence deletion | 78 | 26 | 25 | 59 | 99 | 20 | 12 |
| Percentage | 7.5% | 8.6% | 17.2% | 15.9% | 23.4% | 4.2% | 12.1% |
| 3.1.3 PMI positive events with any target site modification | 99 | 40 | 31 | 92 | 141 | 27 | 14 |
| Percentage | 9.6% | 13.3% | 21.4% | 24.9% | 33.3% | 5.6% | 14.1% |
| Donor (PMI) negative events (escapes) | 181 | 68 | 32 | 219 | 52 | 186 | 21 |
| Escapes frequency | 14.9% | 18.4% | 18.1% | 37.2% | 10.9% | 28.0% | 17.5% |
| 4.3 Total number of escapes with mutations at the target site | 109 | 44 | 34 | 131 | 146 | 34 | 16 |
| Percentage | 9.0% | 11.9% | 19.2% | 22.2% | 30.7% | 5.1% | 13.3% |

It should be understood that the examples and embodiments described herein are for illustrative purposes only and that various modifications or changes in light thereof of the description will be suggested to persons skilled in the art and are to be included within the spirit and purview of this application and the scope of the appended claims.

All publications and patent applications mentioned in this specification are indicative of the level of skill of those skilled in the art that this invention pertains. All publications and patent applications are herein incorporated by reference to the same extent as if each individual publication or patent application was specifically and individually indicated to be incorporated by reference.

What is claimed is:

1. An engineered *Agrobacterium tumefaciens* cell comprising a Chry5 strain chromosomal background and a fully disarmed pTiChry5 vector, wherein the disarmed pTiChry5 vector has both TL-DNA and TR-DNA regions removed, wherein the fully disarmed pTiChry5 vector comprises a nucleic acid sequence at least 90% identical to SEQ ID NO: 3.

2. An engineered *Agrobacterium tumefaciens* cell comprising a Chry5 strain chromosomal background and a fully disarmed pTiChry5 vector, wherein the disarmed pTiChry5 vector has both TL-DNA and TR-DNA regions removed, wherein the fully disarmed pTiChry5 vector comprises a nucleic acid sequence at least 70% identical to SEQ ID NO: 3.

3. An engineered *Agrobacterium tumefaciens* cell comprising a Chry5 strain chromosomal background and a fully disarmed pTiChry5 vector, wherein the disarmed pTiChry5 vector has both TL-DNA and TR-DNA regions removed, wherein a representative sample of said engineered *Agrobacterium tumefaciens* cell is deposited as ATCC Accession No. PTA-124005.

4. A variant or mutant of the engineered *Agrobacterium tumefaciens* cell of claim 1, wherein the variant or mutant cell comprises a fully disarmed pTiChry5 plasmid comprising the nucleic acid sequence of SEQ ID NO: 3.

5. The variant or mutant cell of claim 4, wherein the variant or mutant cell has a mutation in its bacterial chromosome.

6. The variant or mutant cell of claim 5, wherein the mutation is in a gene on the bacterial chromosome or wherein the mutation is an insertion in the bacterial chromosome.

7. The engineered *Agrobacterium tumefaciens* cell of claim 1, further comprising at least one additional nucleic acid molecule, wherein the at least one additional nucleic acid molecule is a booster plasmid, helper plasmid, virulence-enhancing plasmid, and/or a binary vector.

8. A method for producing a transgenic host cell comprising the steps of:
 (a) providing the engineered *Agrobacterium tumefaciens* cell of claim 1, further comprising a transgenic T-DNA region; and
 (b) contacting said engineered *Agrobacterium tumefaciens* cell with a host cell, under conditions that permit the *Agrobacterium* cell to transform the host cell.

9. The method of claim 8, wherein the host cell is a plant cell.

10. The method of claim 9, wherein said plant cell is a cell from a plant tissue selected from the group consisting of: embryogenic plant tissue, organogenic plant tissue, vegetative plant tissue, callus tissue, and reproductive tissue; or wherein the plant cell is a cell from a plant part selected from the group consisting of: pollen, ovule, immature plant embryo, mature plant embryo, seed, seedling, root, cotyledon, stem, node, internode, bud, leaf, shoot apical meristem, floral meristem, flower bud, inflorescence, and cultured plant material.

11. The method of claim 9, wherein said plant cell is a dicotyledonous plant cell.

12. The method of claim 11, wherein said dicoytyledonous plant cell is from soybean (*Glycine max*).

13. The method of claim 9, wherein said plant cell is a monocotyledonous plant cell.

14. The method of claim 13, wherein said monocotyledonous plant is maize.

15. The method of claim 8, wherein the transgenic T-DNA region comprises at least one plant-expressible gene of interest and/or at least one regulatory gene of interest and/or a nucleic acid molecule encoding for at least one genome editing nuclease.

16. A method for modifying a target site in the genome of a host cell, comprising using the engineered *Agrobacterium tumefaciens* cell of claim 1 to introduce into the host cell:
 (a) a first nucleic acid comprising at least 16 contiguous nucleotides, wherein the at least 16 contiguous nucleotides have at least 90% identity with a target site in the genome of the host cell, and further comprising a transgene; and
 (b) a second nucleic acid molecule comprising a nucleotide sequence encoding a nuclease for site-directed cleavage at a nuclease cleavage site in the genome of the host cell adjacent to the nucleotide sequence in the genome of the host cell that corresponds to the at least 16 contiguous nucleotides of (a),
under conditions wherein expression of the second nucleic acid molecule can produce the nuclease and the nuclease can cleave at the nuclease cleavage site in the genome of the host cell and modify the target site in the genome of the host cell.

17. The method of claim 16, wherein the target site in the genome comprises at least a fragment of a native gene and wherein the first nucleic acid molecule comprises a donor DNA molecule, which comprises at least 16 contiguous nucleotides at least 90% identical to a genomic nucleic acid sequence, and further comprises a modified nucleic acid molecule comprising a nucleic acid sequence modified from the native gene; whereby the modified nucleic acid molecule is integrated at the target site in the genome of the host cell.

18. The method of claim 16, wherein the host cell is a plant cell.

* * * * *